United States Patent [19]

Hagiwara

[11] Patent Number: 5,471,066
[45] Date of Patent: Nov. 28, 1995

[54] DEFECT INSPECTION APPARATUS OF ROTARY TYPE

[75] Inventor: Tsuneyuki Hagiwara, Kawasaki, Japan

[73] Assignee: Nikon Corporation, Tokyo, Japan

[21] Appl. No.: 294,990

[22] Filed: Aug. 24, 1994

[30] Foreign Application Priority Data

Aug. 26, 1993 [JP] Japan .................................. 5-211245
Sep. 13, 1993 [JP] Japan .................................. 5-226866

[51] Int. Cl.$^6$ ................................................. G01N 21/88
[52] U.S. Cl. ........................... 250/559.48; 356/237
[58] Field of Search .................................. 250/572, 562, 250/563; 356/237, 429, 430; 382/30, 31

[56] References Cited

U.S. PATENT DOCUMENTS

| | | | |
|---|---|---|---|
| 4,330,775 | 5/1982 | Iwamoto et al. | 356/237 |
| 5,172,000 | 12/1992 | Scheff et al. | 356/237 |
| 5,264,912 | 11/1993 | Vaught et al. | 356/237 |
| 5,274,434 | 12/1993 | Morioka et al. | 356/237 |
| 5,276,498 | 1/1994 | Galbraith et al. | 356/237 |
| 5,377,002 | 12/1994 | Malin et al. | 250/572 |
| 5,389,794 | 2/1995 | Allen et al. | 250/572 |

*Primary Examiner*—Edward P. Westin
*Assistant Examiner*—Steven L. Nichols
*Attorney, Agent, or Firm*—Shapiro and Shapiro

[57] ABSTRACT

A simple signal processing system is utilized to detect defects on the surface of a substrate formed with a circuit pattern at high speed. Light flux from a light source illuminates an inspection point P on the wafer. The light flux from the inspection point P passes a Fourier transform lens and forms a Fourier transform spectrum of the circuit pattern on the inspection point P in the rear focal plane. From the Fourier transform spectrum, a Fourier transform spectrum including no defect information is eliminated by a spatial filter and thereafter the light flux is received by a photoelectric converting device. While the wafer is rotated by a turn table and shifted in a y direction, the spatial filter is rotated in synchronism with rotation of the wafer.

8 Claims, 16 Drawing Sheets

DEFECT INSPECTION APPARATUS OF ROTARY TYPE

BACKGROUND OF THE INVENTION

1. Field of Invention

The present invention relates to a defect inspection apparatus to be used for detecting defects of a circuit pattern formed on a surface of, e.g., a semiconductor device.

2. Related Background Art

Conventionally, a defect inspection apparatus has been used to detect the positions and sizes of defects of a circuit pattern formed on a surface of, e.g., a semiconductor device.

Referring to FIG. 25 showing a conventional defect inspection apparatus, a circuit pattern 2 formed on a surface 1a of a wafer 1 is to be detected and the wafer 1 is disposed on a XY-stage 3. The XY-stage 3 is constructed of a X-stage for shifting the wafer 1 in a x direction parallel to the paper of FIG. 25 within a two-dimensional plane and a Y-stage for shifting the wafer 1 in a y direction perpendicular to the paper of FIG. 25 within the two-dimensional plane.

A light source 4 such as a halogen lamp is disposed above the wafer 1. Light flux 5 emitted from the light source 4 is condensed by a collimeter lens 6 to be light flux 7, which then is incident on a beam splitter 8. Light flux 9 reflected by the beam splitter 8 illuminates a predetermined illumination area on the surface 1a of the wafer 1. Of light reflected from the surface 1a of the wafer 1, light flux 10 transmitted through the beam splitter 8 enters an imaging lens 11. The imaging lens 11 is disposed such that its object plane coincides with the surface 1a of the wafer 1 and an image of the circuit pattern on the wafer within the illumination area is formed on an image plane 12 of the imaging lens 11.

A two-dimensional image pick-up device 12 is provided to the image plane 12 such that its image pick-up surface coincides with the image plane 12. The image pick-up device 12 converts the image of the circuit pattern photoelectrically to obtain an image signal S1, which is output to a signal processor 14. In the meantime, a data storing section 15 supplies to the signal processor 14 a reference signal S2 corresponding to design data of a circuit pattern with no defect (nonerroneous circuit pattern). The signal processor 14 compares the image signal S1 with the reference signal S2 to obtain the presence or absence of defects of the circuit pattern on the surface 1a of the wafer 1, the sizes and positions of defects thereof. Defect information S3 of the circuit pattern is supplied from the signal processor 14 to a display 16, which displays the sizes and positions of defects of the circuit pattern on its screen.

In the above prior art, the processor 14 needs to perform a complex image processing at high speed so as to obtain the sizes and positions of the defects of the circuit pattern. Therefore, a high-speed computer is required as the signal processor 14 and the signal processing system becomes large.

For the purpose of solving this problem, there is another defect inspection apparatus in which a laser beam is converged on a small inspection area on the surface 1a of the wafer 1 without illuminating the large illumination area on the surface 1a of the wafer 1 and the wafer 1 is scanned linearly by the laser beam converged on the small illumination area by the use of an optical scanner (galvanomirror or the like) as an optical deflecting system. However, in the optical scanner, a mirror is oscillated to scan the laser beam, so that the inspection speed is limited owing to the upper limit of a scan rate and as a result, it takes a long time to inspect the entire surface of the wafer 1.

SUMMARY OF THE INVENTION

It is therefore an object of the present invention to provide a rotary type defect inspection apparatus capable of detecting defects of a surface of a substrate formed with a circuit pattern by the use of a simple signal processing system at high speed.

A rotary type defect inspection apparatus of the present invention for detecting defects on a surface of a substrate with a predetermined pattern formed thereon has illuminating means for emitting light flux for inspection to a predetermined inspection area on the surface of the substrate; a Fourier transform optical device for performing Fourier transform of the light flux reflected from the substrate; a spatial filter disposed in the vicinity of a Fourier transform plane caused by the Fourier transform optical device, a portion of the spatial filter coinciding with a bright portion of a Fourier transform pattern of a nonerroneous reference pattern obtained by forming the circuit pattern on the substrate so as to have no defect being made to be a light-shielding portion; and photoelectric converting means for converting light flux passed through the spatial filter photoelectrically.

According to the present invention, without utilizing an optical scanner, by rotating the substrate placed on a turn table at high speed and shifting the substrate by shifting means, the surface of the substrate is scanned by the round area of light at high speed. Therefore, the inspection speed will not be limited by the optical scanner or the like.

Also, in this embodiment, Fourier transform of the light flux from the substrate is performed. And, from its Fourier transform pattern, components of the Fourier transform pattern of a nonerroneous reference pattern with no defect are eliminated by the spatial filter, so that only defect information is extracted optically. Therefore, burden of a signal processing system for processing electric signals after photoelectric conversion is reduced and the structure of the signal processing system is simplified. Also, the inspection speed will not be limited by the processing speed of the signal processing system. At this time, as the Fourier transform pattern of the pattern on the substrate is rotated in accordance with rotation of the substrate, the spatial filter is rotated in synchronism with rotation of the substrate in order to constantly extract the defect information only.

In this case, even though the substrate rotates, the position of the zero-order component of the Fourier transform pattern of the pattern on the substrate is not changed. Therefore, the shaft of the spatial filter is preferably set to the position of the zero-order light component.

Also, when the Fourier transform optical device is formed of a plurality of optical fiber bundles, the Fourier transform optical device can be brought near the substrate and the light condensing efficiency of the light flux from the substrate is improved.

A rotary type defect inspection apparatus of the present invention for detecting defects on a surface of a substrate with a predetermined pattern formed has illuminating means for emitting light flux for inspection to a predetermined inspection area on the surface of the substrate; a Fourier transform optical device for decomposing the light flux reflected from the substrate into spatial frequency components; a set of photoelectric converting means for receiving the light flux of the spatial frequency components generated by the Fourier transform optical device in light receiving surfaces of a predetermined size and converting it photoelectrically; a turn table for rotating the substrate centered on a shaft parallel to an optical axis of the Fourier transform optical device; and shifting means for shifting the substrate in a plane perpendicular to the optical axis of the Fourier transform optical device, wherein the surface of the substrate is scanned in the predetermined inspection area spirally by rotating and shifting said substrate by the turn table and the shifting means respectively, and defects of the predetermined pattern on the substrate are detected by a signal having a minimum level among photoelectric conversion signals output from the set of photoelectric converting means.

In this embodiment, the light flux of the spatial frequency component obtained by performing Fourier transform of the light flux from the substrate is converted by the set of photoelectric converting means. In this case, the bright portions of the spectrums of the circuit patterns with no defect formed on the substrate are distributed discretely while the spectrum of the light flux from a defect portion on the substrate is distributed widely with an approximately uniform level. Therefore, in the present invention, when a signal with a minimum level among photoelectric conversion signals from the set of photoelectric converting means exceeds, e.g., a predetermined threshold, it is judged that there are defects. Thereby, complex signal processing is not required and defect detection can be per, formed at high speed.

Also, when the light/flux of the spatial frequency component generated by the Fourier transform optical device is led to the set of photoelectric converting means via a set of optical fiber bundles, it is possible to utilize a large photoelectric detecting device such as a photomultiplier and the resolution of the spatial frequency component can be maintained highly.

BRIEF DESCRIPTION OF THE DRAWINGS

FIG. 24B is a diagram showing another method of dividing the Fourier spectrum area 33a.

DETAILED DESCRIPTION OF THE PREFERRED EMBODIMENTS

A rotary type defect inspection apparatus according to a first embodiment of the present invention will be described with reference to FIGS. 1 to 4 now.

Figure 1:
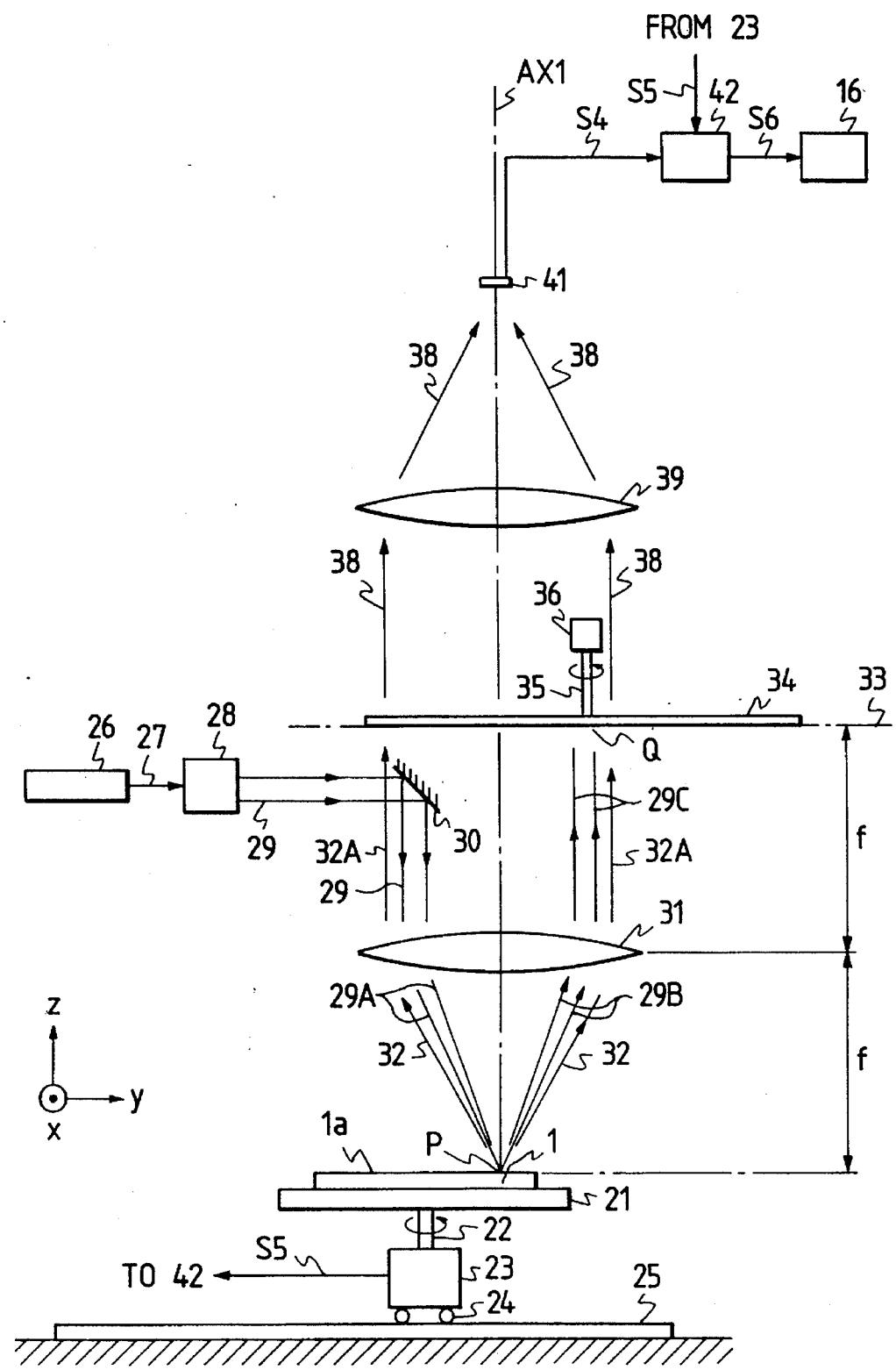
FIG. 1 is a schematic view showing the structure of a rotary defect inspection apparatus according to a first embodiment of the present invention.

FIG. 1 shows the rotary type defect inspection apparatus of this embodiment. A wafer 1 with a circuit pattern formed on its surface is disposed on a turn table 21 by means of vacuum adsorption. A shiftable rotating section 23 rotates the turn table 21 via a shaft 22. When the Y-axis is taken in a direction parallel to the paper of FIG. 1 and the X-axis is taken in a direction perpendicular to the paper of FIG. 1, the turn table 21 rotates the wafer 1 in a state that a surface 1a of the wafer 1 is constantly kept parallel to the xy-plane defined by the X-axis and the Y-axis. The shiftable rotating section 23 is disposed via rollers 24 on a rail 25 extending in the y direction. As the shiftable rotating section 23 drives the rollers 24 to rotate, the shiftable rotating section 23 is shifted along the rail 25 in the y direction.

Above the turn table 21 is disposed a light source 26 such as a He-Ne laser light source or the like for emitting a coherent light flux (laser beam, etc.). Light flux 27 emitted from the light source 26 is made a parallel light flux 29 having a round shape in section by means of a beam expander 28. The parallel light flux 29 is reflected by a mirror 30 and directed to a Fourier transform lens 31. Then, light flux 29A condensed by the Fourier transform lens 31 illuminates an inspection point P on the wafer 1 in the form of a spot. The diameter of the illumination area by the light flux 29a illuminating the inspection point P is, e.g., 40 µm and the illuminance of the illumination area is set to be a desired value.

The Fourier transform lens 31 is disposed such that its effective center is positioned at the distance of a focal length f from the surface 1a of the wafer 1. An optical axis AX1 of the Fourier transform lens 31 is parallel to the Z-axis perpendicular to the xy-plane. Light flux 32 emanated from the inspection point P due to the illumination of the light flux 29A enters the Fourier transform lens 31. Light flux 32A passed through the Fourier transform lens 31 forms, on its rear focal plane 33 (Fourier transform plane), a selectively filterable Fourier transform pattern (Fourier spectrum) of the circuit pattern on the inspection point P on the wafer 1.

Also, light flux 29B directly reflected by the surface 1a of the wafer 1 due to the illumination of the light flux 29 again enters the Fourier transform lens 31 to be light flux 29C having the same cross-sectional shape as the parallel light flux 29 reflected by the mirror 30. The light flux 29C forms a circular spectrum on the rear focal plane 33 with a point Q as its center. The point Q is the position of the zero-order light component. A rotatable spatial filter 34 is provided on the rear focal plane 33. The rotatable spatial filter 34 is in the shape of a disk and connected to a rotating section 36 via a shaft 35. The rotating section 36 rotates via the shaft 35 the spatial filter 34 centered on the point Q within the rear focal plane 33. The spatial filter 34 rotates in synchronism with the wafer 1 at the same angular speed as that of the wafer 1. The respective rotation directions of the wafer 1 and the spatial filter 34 need to be constantly the same, but both relative rotation directions may be the same or opposite.

In the spatial filter 34, when the light flux 29A illuminates the circuit pattern on the surface of the wafer 1 with no defect, i.e., a nonerroneous circuit pattern, portions coinciding with bright portions of a Fourier transform pattern formed on the rear focal plane 33 by the light flux emanated from the nonerroneous circuit pattern is made opaque and the other portion is made transparent. That is, the spatial filter 34 hinders the Fourier transform pattern (Fourier spectrum) of the nonerroneous circuit pattern from filtering therein.

The spatial filter 34 can be formed, e.g. in the following manner. First, a photographic dry plate is positioned on the rear focal plane 33 and a master wafer formed with a nonerroneous circuit pattern is placed on the turn table 21. Then, while rotating the master wafer and the photographic dry plate synchronously, the photographic dry plate is exposed by the Fourier transform pattern generated from the master wafer to obtain the spatial filter 34. When it is difficult to obtain the nonerroneous circuit pattern, the spatial filter 34 is formed in the following manner.

Figure 2:
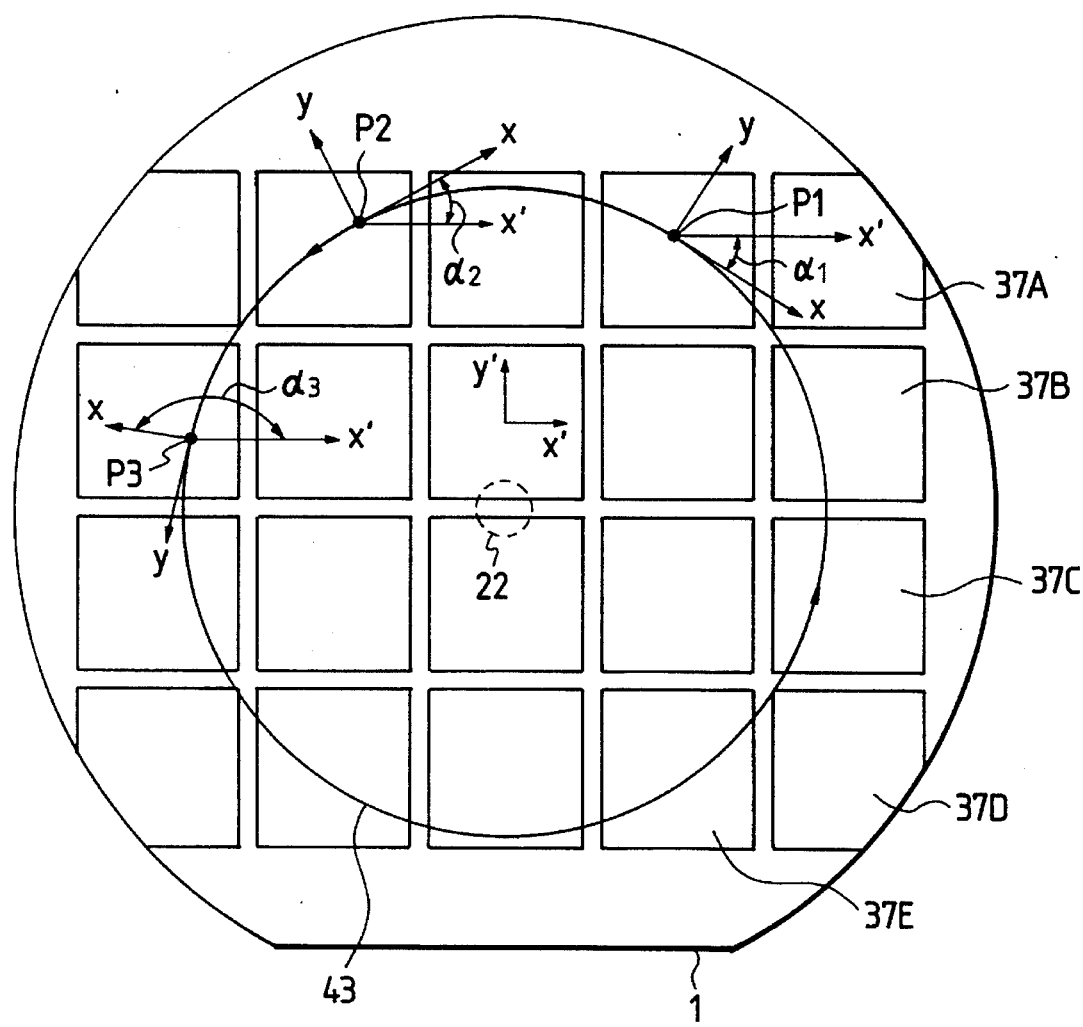
FIG. 2 is an enlarged plan view showing an inspection area on the wafer 1 of FIG. 1.

That is, the surface of the wafer 1 has a plurality of pattern units 37A, 37B, 37C, . . . having the same circuit, as shown in FIG. 2. Then, although all the pattern units have respective defect portions, it can be deemed that the positions of the defect portions are different from each other and the area of the defect portions is significantly small as compared to the area of the nonerroneous portions of all the pattern units. Therefore, the energy of the light flux 29A is sufficiently reduced such that the photographic dry plate will not be exposed by a light pattern formed by the light flux 29A being incident on the defect portions. Then, the resultant light flux 29A is sequentially directed to the plurality of pattern units on the wafer 1 to form a light pattern from the nonerroneous circuit pattern with the large area. As a result, the photographic dry plate is exposed only by the light pattern from the nonerroneous circuit pattern. According to this method, naturally, the amount of exposure with respect to the photographic dry plate can be controlled by changing the speed for shifting the illumination area on the wafer 1. The photographic dry plate exposed by the light pattern formed from the nonerroneous circuit pattern is subjected to development to be the spatial filter 34. The obtained spatial filter 34 is mounted to the rear focal plane 33 such that the relative angular relationship between the spatial filter 34 and the wafer 1 becomes the same as at the time of exposure (formation) of the spatial filter 34.

The spatial filter 34 may be formed by a liquid crystal display device (LCD), a SLM (Spatial Light Modulator) device such as an electrochromic device (ECD) other than the photographic dry plate. When utilizing these, it is preferable to previously measure the opaque portion to be formed on the spatial filter 34 so as to correspond to the Fourier transform pattern of the nonerroneous circuit pattern by disposing a two-dimensional image pick-up device in the rear focal plane 33, but it is possible to obtain the opaque portion by performing Fourier transform of the design data of the circuit pattern by a computer and simulating them. Also, the spatial filter 34 can be formed more simply by recording a predetermined pattern on a transparent film by the use of a known plotter for a computer. In this case, the recording data can be obtained by the above-mentioned method too.

In FIG. 1, in accordance with the operation of the shiftable rotating section 23, the wafer 1 is shifted in the y direction while being rotated around the shaft 22. Owing to this operation, the round area of light on the inspection point P due to the light flux 29A relatively rotates on the wafer 1 spirally to scan the wafer 1 thereby to detect defects of the entire surface of the wafer 1 at high speed.

In this embodiment, when performing the rotational scanning of the wafer 1, the spatial filter 34 is rotated in synchronism with the rotation of the wafer 1 around the position Q of the zero-order light component of the Fourier spectrum formed on the rear focal plane 33. That is, while rotating the wafer 1, the filtering of the Fourier spectrum is performed to detect defects. Therefore, defect information carrying light flux 38 which is light flux passed through the spatial filter 34 includes only defect information of the circuit pattern on the inspection point P on the wafer 1. The defect information carrying light flux 38 is condensed on the light receiving surface of a photoelectric converting device 41 by a condensing lens 39. A detect signal S4 obtained by the photoelectric converting device 41 is supplied to a signal processor 42. Also, position information S5 for representing the two-dimensional coordinates of the inspection point P on the wafer 1 is supplied to the signal processor 42 from the shiftable rotating section 23.

The signal processor 42 has a threshold whose level is larger than the electrical and optical noise level and extracts the defect signal 4 whose level is equal to or larger than the threshold as a detect. In this embodiment, as the Fourier transform pattern of the nonerroneous reference pattern is stopped to filter by the spatial filter 34, the light flux passed through the spatial filter 34 is regarded as the light flux from defect portions and the optical noise light. When the signal level of the defect signal S4 is equal to or more than the threshold, the circuit pattern on the inspection point P is regarded as a defect portion. Also, the signal processor 42 detects the magnitude of the signal level of the defect portion and determines it as the size of the defect portion. Further, the signal processor 42 detects the position of the defect portion of the wafer 1 based on the above position information S5. The signal processor 42 supplies display information S6 representing the positions and sizes of defect portions to a display 16. The display 16 displays the positions of the defect portions by the map indication and the sizes of the corresponding defect portions. At this time, depending on the circuit pattern on the wafer 1, there is a case that the Fourier transform spectrum of the nonerroneous circuit pattern is not equalized on the disk-like spatial filter 34. In this case, when the spatial filter 34 is rotated, the light energy of the defect information carrying light flux 38 received by the photoelectric converting device 41 is modulated. This energy modulation affects the detection of the defect portions and the discrimination of the sizes. This energy modulation is in synchronism with the rotation of the spatial filter 34. Therefore, in order to remove the influence of the energy modulation, a plain wafer is placed on the turn table 21 and a sample for correcting a defect portion such as a dust particle to be a reference is applied to the plain wafer or a light source for correction is provided in a position conjugate to the wafer 1. Then, the energy modulation of the output signal from the photoelectric converting device 41 is measured as a function of the rotation angle of the spatial filter 34. Thereafter, in the signal processor 42, the defect signal S4 is intensively modulated so as to cancel the energy modulation by the use of that measurement result. Thereby, the entire surface of the wafer 1 can be inspected with the same sensitivity.

Next, a relationship between the inspection point P on the wafer 1 and the Fourier spectrum will be described. FIG. 2 shows the region on the wafer to be inspected. In FIG. 2, the surface of the wafer 1 is formed with the plurality of pattern units 37A, 37B, 37C . . . having the same circuit patterns in a matrix form. In FIG. 2, when inspecting an inspection point P1 on the wafer 1, a rectangular coordinate system (x', y') (hereinafter referred to as "reference coordinate system") being the reference to form the circuit patterns of the plurality of pattern units 37A, 37B, . . . on the wafer 1 and a coordinate system (x, y) of the apparatus in FIG. 1 form an angle $\alpha_1$. In this case, when the wafer 1 rotates around the shaft 22, and when the inspection point of the wafer 1 is moved to an inspection point P2 and an inspection point P3, the reference coordinate system (x', y') and the coordinate system (x, y) of the apparatus form an angle $\alpha_2$ and an angle $\alpha_3$ respectively.

Figure 3A:
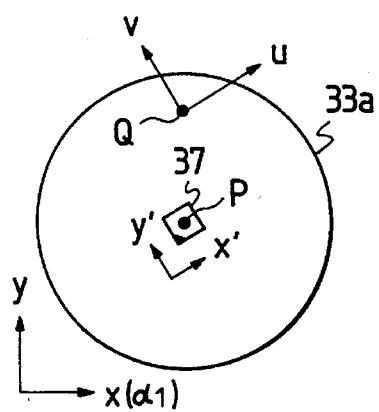
FIGS. 3A to 3C are explanatory diagrams showing states of Fourier spectrums when the angle formed by the reference coordinate system (x', y') and the coordinate system (x, y) of the apparatus is changed in the first embodiment.
Figure 3B:
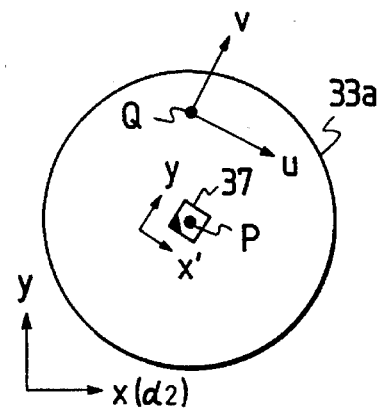
Figure 3C:
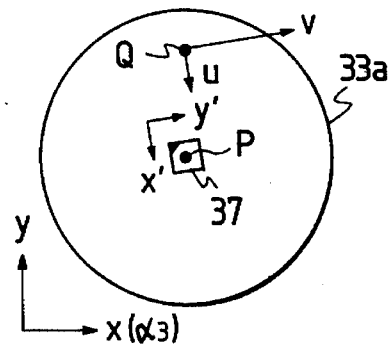

FIGS. 3A to 3C each show a spectrum area 33a limited by the aperture of the Fourier transform lens 31 on the rear focal plane (Fourier transform surface) 33 of the Fourier transform lens 31 of FIG. 1. In FIG. 3A, the reference coordinate system (x', y') of one pattern unit 37 on the inspection point P (actually positioned on the object plane of the Fourier transform lens 31) on the wafer 1 and the coordinate system (x, y) of the apparatus form the angle $\alpha_1$. At this time, a spatial frequency spectrum observed within the spectrum area 33a becomes a portion on a coordinate system (u, v) parallel to the reference coordinate system (x', y') with the position Q of the zero-order light component as its origin. As the angle formed by the reference coordinate system (x', y') of the pattern unit 37 and the coordinate system (x, y) of the apparatus is changed to $\alpha_1$, $\alpha_2$ and $\alpha_3$, the observable spectrum area 33a is rotated around the position Q of the zero-order light component on the coordinate system (u, v). When observed from the apparatus side (the coordinate system (x, y) of the apparatus), it is seen that the spatial frequency spectrum observed in the spectrum area 33a is rotated around the inspection point P in synchronism with the rotation of the pattern unit 37, as shown in FIGS. 3A, 3B and 3C.

Figure 4:
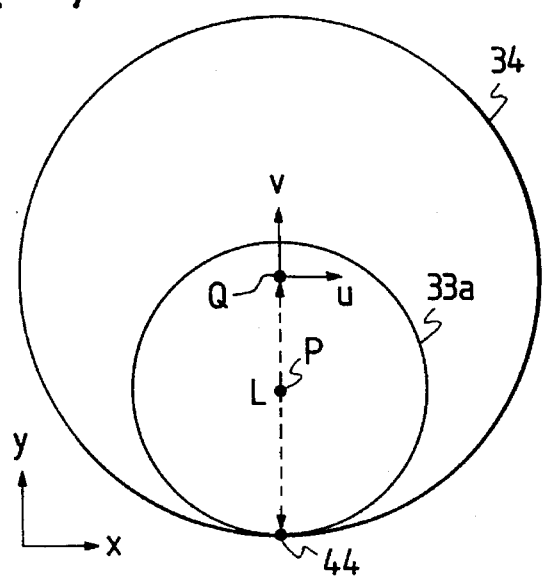
FIG. 4 is a plan view showing the spatial filter 34 and the spectrum area 33a of the first embodiment.

Therefore, when the inspection point P1, P2, P3, : . . is shifted on a circular scanning line 43 to detect defects of the circuit patterns within the plurality of pattern units (37A, 37B, etc.) because of the rotation of the wafer 1 as shown in FIG. 2, the spatial filter 34 for rotating in synchronism with the rotation of each pattern unit is required, as shown in FIG. 4. In FIG. 4, the center of the rotation of the spatial filter 34 is the position Q, and the radius L of the spatial filter 34 is determined to be the distance from the position Q to the furthest point 44 within the spectrum area 33a.

According to the above-mentioned embodiment, the defect inspection is carried out on the entire surface of the wafer 1 at high speed by relatively rotating and scanning the inspection point P on the wafer 1. Also, as the Fourier transform pattern of the circuit pattern on the wafer 1 rotates owing to the rotation of the wafer 1, the spatial filter 34 which rotates in synchronism with the rotation of the wafer 1 is utilized to prevent the Fourier transform spectrum from the nonerroneous reference pattern from filtering through the spatial filter 34 and the defect information carrying light flux 38 passed through the spatial filter 34 is detected to find defects. Therefore, in the signal processing system, it is sufficient to compare the defect signal S4 to the predetermined threshold and to maintain the value of the detect signal S4 in a defect section. Therefore, a large computer or the like is not required, so the structure of the signal processing system is simple and the processing speed is high.

Figure 5:
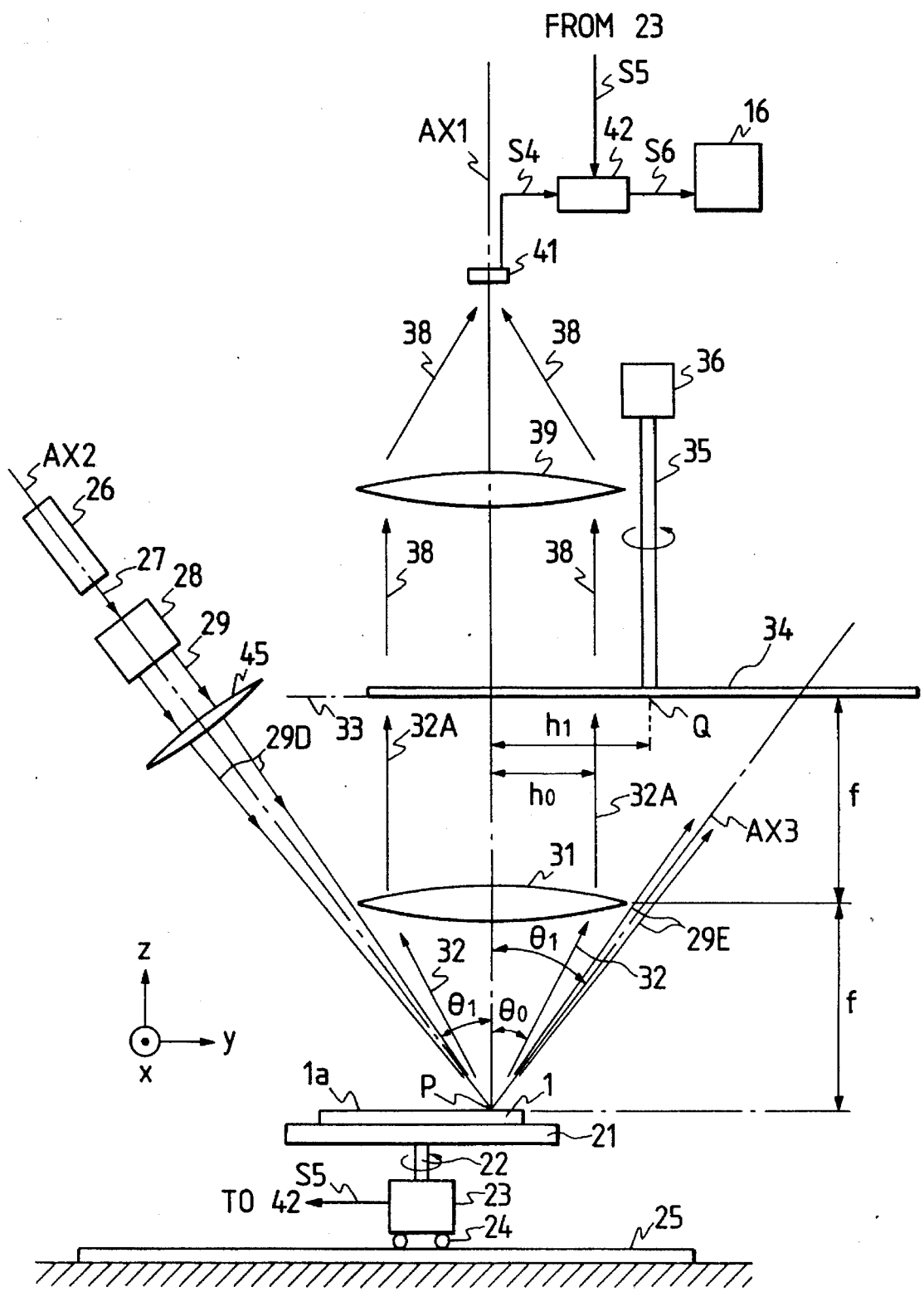
FIG. 5 is a schematic view showing the structure of a rotary defect inspection apparatus according to a second embodiment of the present invention.

Next, a second embodiment of the present invention will be described with reference to FIG. 5. In FIG. 5, elements corresponding to those in FIG. 1 are designated by the like reference numerals and the detailed description thereof will be omitted.

FIG. 5 shows a rotary type defect inspection apparatus of the second embodiment. In FIG. 5, the wafer 1 formed with the circuit pattern is placed on the turn table 21, which is connected via the shiftable rotating section 23 to the shaft 22. Due to the operation of the shiftable rotating section 23, the wafer 1 is shifted in the y direction while rotating around the shaft 22. Thereby, in a similar manner to the first embodiment, the round area of light illuminating the inspection point P relatively rotates on the wafer 1 spirally to scan it, whereby the defect inspection is performed at high speed on the entire surface of the wafer 1.

The light source 26 is provided above the turn table 21. The light flux emitted from the light source 26 becomes the parallel light flux 29 having a circular cross-sectional shape by the beam expander 28 and enters a condensing lens 45. Light flux 29D converged by the condensing lens 45 illuminates the inspection point P on the wafer 1 with, e.g., a diameter of 30 μm. The Fourier transform lens 31 is disposed above the wafer 1. The effective center of the Fourier transform lens 31 is positioned in a plane at the focal length f from the surface 1a of the wafer 1.

Light flux 32 emitted from the inspection point P owing to the light flux 29D enters the Fourier transform lens 31. Light flux 32A passed through the Fourier transform lens 31 forms a selectively filterable Fourier spectrum on the rear focal plane 33.

The Fourier transform lens 33 has a characteristic that in a relationship between the image height h by the incident light flux and the angle 8 formed by the light flux and the optical axis AX1, the height h of the image is proportional to f·sin θ. The Fourier transform lens 31 is assumed to have a characteristic that, e.g., h=f·sin θ. The light flux 32 enters the Fourier transform lens 31 at an angle $\theta_0$ with respect to the optical axis AX1 and illuminates a round area on the rear focal plane 33 where the image height $h_0$ is f·sin $\theta_0$. If the optical axis AX2 of the illumination system including the light source 26 and the condensing lens 45 is AX2 and the optical axis AX2 intersects the optical axis AX1 at an angle $\theta_1$, the optical axis AX3 of light flux 29E directly reflected from the surface of the wafer 1 owing to the light flux 29D intersects the optical axis AX1 at the angle $\theta_1$.

In this embodiment, as the aperture of the Fourier transform lens 31 is not large enough for the light flux being at the angle $\theta_1$ with respect to the optical axis AX1 to enter, it is impossible to measure the spatial frequency spectrum of the light flux 29E on the rear focal plane 33. However, as the angle $\theta_1$ is known in advance, it is apparent that a position spaced at a distance $h_1$ (=f·sin $\theta_1$) from the optical axis AX1 is the spectrum position of the light flux 29E (zero-order light). Therefore, in this embodiment, the spatial filter 34 is rotated around the position Q of the image height $h_1$ on the rear focal plane 33 in the paper of FIG. 5. The structure and operation of the spatial filter 34 is the same as in the first embodiment. The Fourier transform pattern of the nonerroneous circuit pattern is stopped to filter by a light-shielding portion of the spatial filter 34, and the other light pattern generated from defect portions on the wafer 1 is transmitted through a light transmitting portion of the spatial filter 34 to be the defect information carrying light flux 38. The other structures are the same as in the first embodiment.

Also, in this embodiment, the Fourier transform pattern from the nonerroneous circuit pattern is stopped by the spatial filter 34 by performing the rotational scanning of the wafer 1 in a similar manner to the first embodiment and rotating the spatial filter 34 in synchronism with the wafer 1. The defect information carrying light flux 38 passed through the spatial filter 34 is converted into the defect signal S4 by the photoelectric converting device 41 and positions and sizes of defect portions are detected at high speed. At this time, in this embodiment, Fourier transform component far away from the zero-order light component as compared to the first embodiment are detected on the rear focal plane 33. Also, since the Fourier transform component from the nonerroneous circuit pattern is intense around the zero-order light component, the component away from the zero-order component is extracted thereby to reduce the influence of the nonerroneous circuit pattern and to enhance the ability for detecting defect portions.

Further, in this embodiment also, depending on the circuit pattern on the wafer 1, there is a case that the Fourier spectrum of the nonerroneous circuit pattern is not equalized on the spatial filter 34, whereby the light energy of the defect information carrying light flux 38 being incident on the photoelectric converting device 41 is modulated when the spatial filter 34 is rotated. The modulation can be canceled in the same manner as in the first embodiment.

Next, a modification of the second embodiment in FIG. 5 will be described with reference to FIG. 6, wherein a set of optical fiber bundles are utilized instead of the Fourier transform lens 31.

Figure 6:
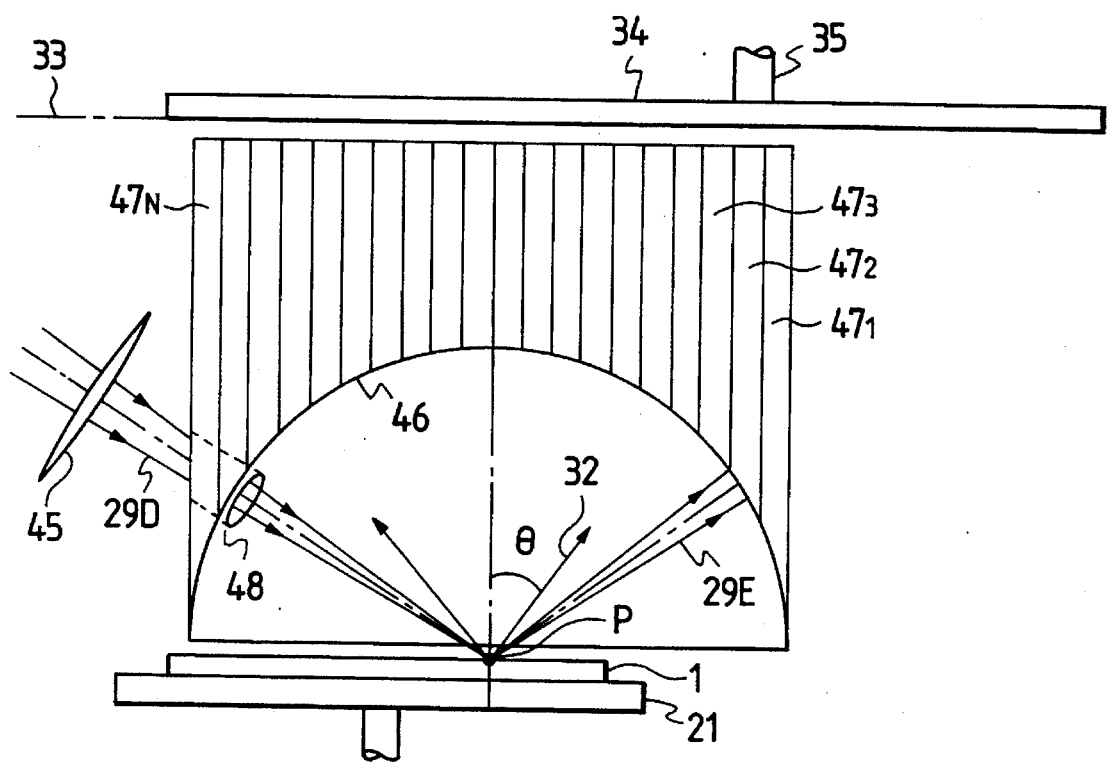
FIG. 6 is a cross section showing an essential portion of a modification of the second embodiment, wherein a set of optical fiber bundles are utilized instead of the Fourier transform lens 31.

FIG. 6 shows an important portion of the modification and elements corresponding to those in FIG. 5 are designated by the like reference numerals. In FIG. 6, respective one-side ends of optical fiber bundles $47_1, 47_2, \ldots, 47_N$ are disposed on a spherical plane 46 with the inspection point P on the wafer 1 as its center. The other-side ends of the optical fiber bundles $47_1, 47_2, \ldots, 47_N$ are disposed on the plane 33 parallel to the surface of the wafer 1 along the normal line with respect to the surface of the wafer 1. The spatial filter 34 is disposed on the surface 33.

The light flux 29D condensed by the condensing lens 45 illuminates the inspection point P on the wafer 1 via an opening 48 being a portion of the spherical plane 46. The light flux 32 from the inspection point P is led to the surface 33 via the optical fiber bundles $47_1, 47_2, \ldots, 47_N$. In this case, if the radius of the spherical plane 46 is R, the image height h of the light flux 32 emanated from the wafer 1 at the angle θ with respect to the normal line is R·sin θ, which is equivalent to the state that Fourier transform of the light flux 32 is performed.

Accordingly, a set of optical fiber bundles $47_1, 47_2, \ldots, 47_N$ perform Fourier transform of the light flux from the circuit pattern of the wafer 1 in a similar manner to the Fourier transform lens 31 of FIG. 5.

Also, the spatial filter 34 is rotated around a position (the position of the zero-order light component) at which the light flux 29E directly reflected by the wafer 1 owing to the light flux 29D passes. Thereby, the Fourier transform component of the nonerroneous circuit pattern from the wafer 1 and the light-shielding portion on the spatial filter 34 corresponding to the Fourier transform component of the nonerroneous circuit pattern will not be displaced from each other. The other structure is the same as in the embodiment of FIG. 5.

In this case, the light flux emanated from the inspection point P on the wafer 1 at the large angle θ with respect to the normal line is also led to the surface 33 via the optical fiber bundles, so the light receiving efficiency is preferable. Also, it is possible to bring the surface of the wafer 1 and the surface 33 near to each other, contributing to miniaturization of the apparatus.

According to the first and second embodiments, the substrate to be inspected is rotated and shifted by the use of the turn table and the shifting means, so that it is possible to perform defect inspection of the whole surface of the substrate at high speed. Also, as the spatial filter is rotated in synchronism with the rotation of the substrate and the Fourier transform component from the nonerroneous reference pattern is stopped to filter, the defect inspection can be performed by only comparing the photoelectric conversion signal from the photoelectric converting means with the predetermined threshold. Therefore, the structure of the signal processing system is simple and the signal processing speed is also high.

Further, when the filter rotating means rotates the spatial filter centered on the position of the zero-order light component of the Fourier transform pattern of the nonerroneous reference pattern, the Fourier transform component from the nonerroneous reference pattern is preferably eliminated.

Furthermore, when the Fourier transform optical device is the plurality of optical fiber bundles whose one-side ends thereof are disposed on the spherical plane with the predetermined inspection area as its center and whose other-side ends thereof are disposed on a similar position to the orthographic projection of their one-side ends to a predetermined plane, it is possible to bring the Fourier transform optical device near the substrate, enabling miniaturization of the apparatus. And, the light flux emanated from the substrate at a large diffraction angle can be received to enhance the light receiving efficiency.

Figure 7:
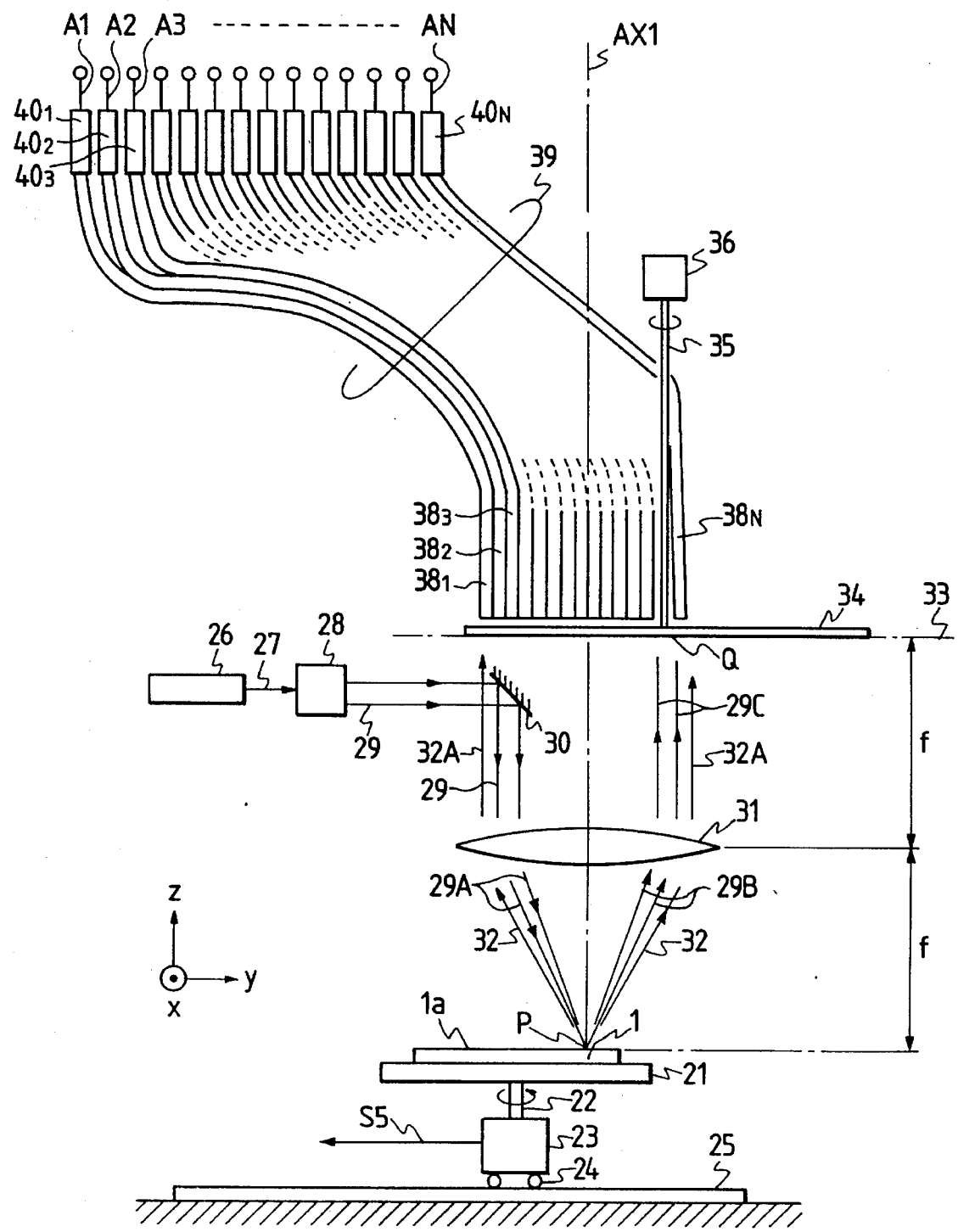
FIG. 7 is a schematic view showing the structure of a rotary defect inspection apparatus according to a third embodiment of the present invention.

Next, a rotary type defect inspection apparatus according to a third embodiment of the present invention will be described with reference to FIG. 2 and FIGS. 7 to 9. FIG. 7 shows the rotary type defect inspection apparatus of this embodiment, wherein elements the same as those in the above embodiments are designated by the like reference numerals.

Figure 13:
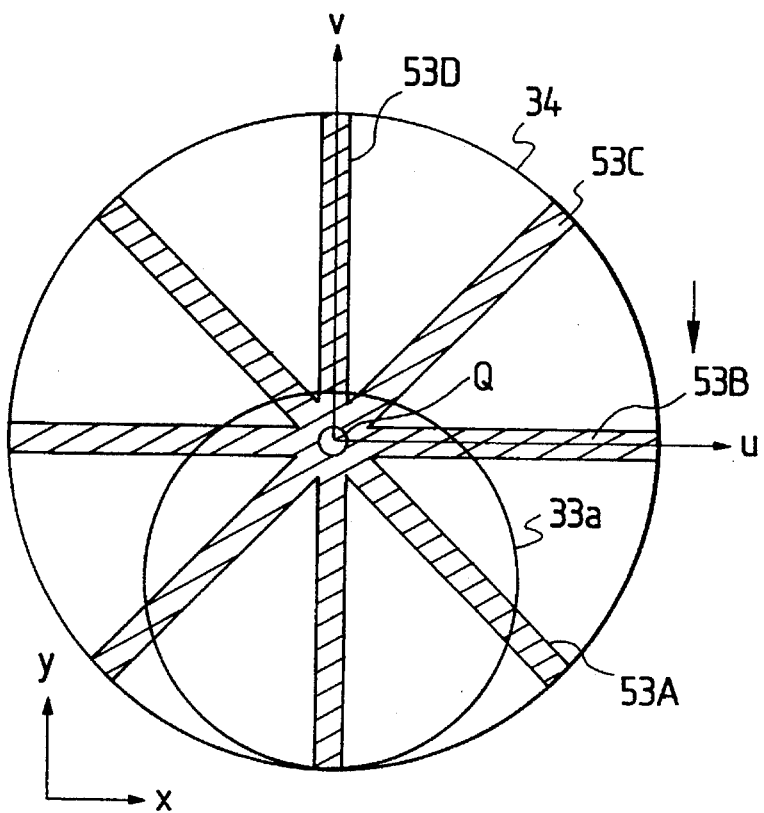
FIG. 13 is a diagram showing the spatial filter 34 having light-shielding zones 53A to 53D for preventing the Fourier transform patterns of linear patterns in various directions from filtering therein.

FIG. 13 shows an example of the spatial filter 34 which is formed of a glass substrate provided with light-shielding zones 53A to 53D formed at 45° intervals thereon. In this embodiment, the spatial filter 34 is commonly used for various circuit patterns. Then, it is not necessary to form the spatial filter 34 for each circuit pattern to be inspected.

The spatial filter 34 can be formed by, e.g., a liquid crystal display device (LCD) or a SLM device such as an electrochromic device (ECD). When utilizing these devices, the pattern of an opaque portion to be recorded on the spatial filter 34 is the same as the pattern of FIG. 13. The spatial filter 34 can be formed by recording a predetermined pattern on a transparent film by the use of a known plotter for a computer.

In FIG. 7, due to the operation of the shiftable rotating section 23, the wafer 1 is shifted in the y direction while being rotated around the shaft 22. Accordingly, the light flux 29A illuminating the inspection point P rotates relatively on the wafer 1 spirally and scans it, whereby defect inspection is performed at high speed over the entire surface of the wafer 1.

In this embodiment, when the rotational scanning of the wafer 1 is performed, the spatial filter 34 is rotated in synchronism with the rotation of the wafer 1 around the position Q of the zero-order light component of the Fourier spectrum formed on the rear focal plane 33 and defect inspection is performed by filtering the Fourier spectrum while rotating the wafer 1. Therefore, the light flux passed through the spatial filter 34 includes the Fourier transform pattern corresponding to the circuit patterns arranged two-dimensionally on the inspection point of the wafer 1 and light information regarding defects of the circuit pattern.

In this embodiment, respective one-side end faces of a set of optical fiber handles $38_1, 38_2, \ldots, 38_N$ (N=a predetermined integer) are disposed close to the upper surface of the spatial filter 34 so as to cover the area of the Fourier transform pattern formed by the Fourier transform lens 31. These optical fiber handles $38_1, 38_2, \ldots, 38_N$ are bundled together by a holding member 39. And, the other-side end faces of the optical fiber handles $38_1, 38_2, \ldots, 38_N$ are joined to the light receiving surfaces of photoelectric converting devices $40_1, 40_2, \ldots, 40_N$. For example, photomultipliers or PIN-silicon photodiodes are utilized for the photoelectric converting devices $40_1, 40_2, \ldots, 40_N$.

The light flux passed through the spatial filter 34 is subjected to the wavefront splitting by the light receiving ends of the optical fiber handles $38_1$ to $38_N$ and transmitted in the optical fiber handles $38_1$ to $38_N$ to be incident on the respective light receiving surfaces of the photoelectric converting devices $40_1$ to $40_N$. The photoelectric converting devices $40_1$ to $40_N$ convert the received light photoelectrically and outputs detection signals A1 to AN. The detection signals A1 to AN are supplied to a signal processing circuit shown in FIG. 8, where the presence or absence of defects are judged.

Figure 8:
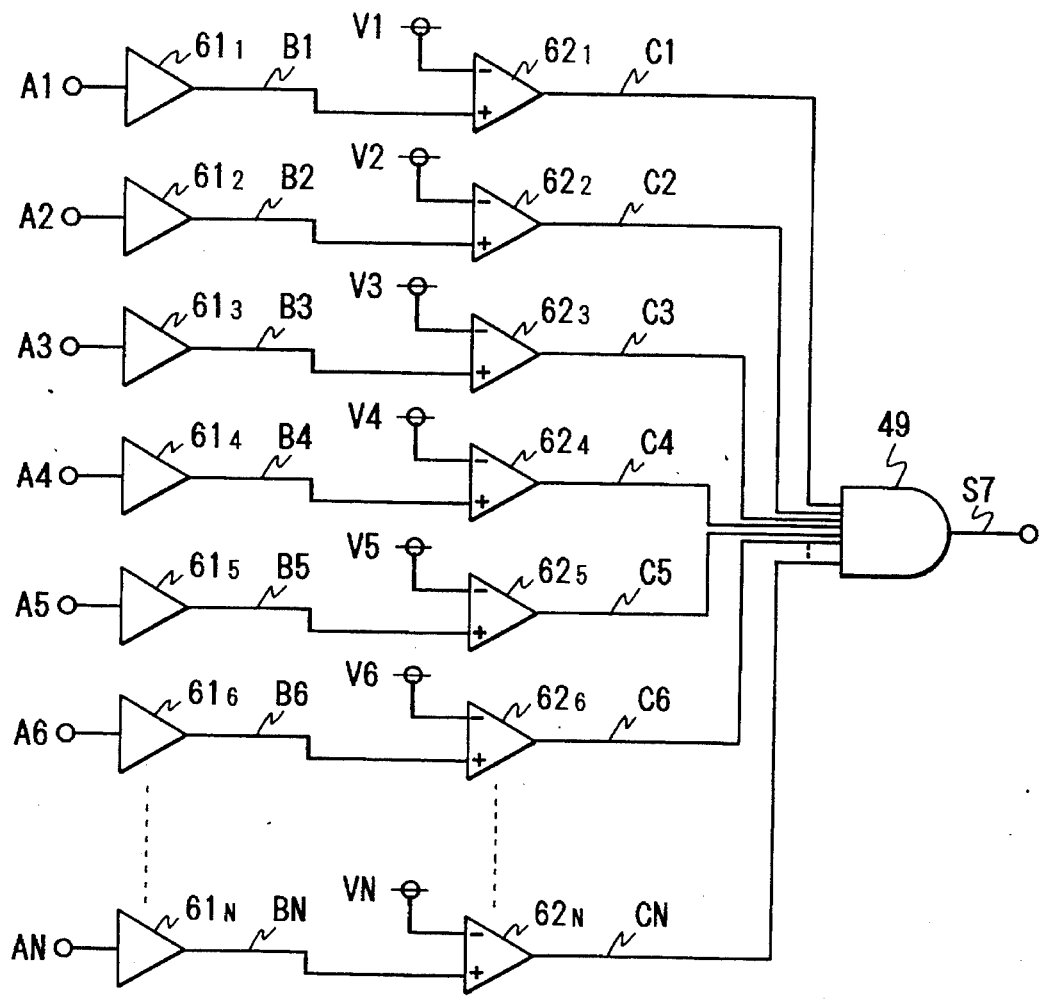
FIG. 8 is a block diagram showing an example of a defect discriminating circuit of a signal processing system in the third embodiment.

FIG. 8 shows a defect discriminating circuit in the signal processing circuit in this embodiment. In FIG. 8, the detection signals A1 to AN pass amplifiers $61_1$ to $61_N$ to become detection signals B1 to BN, which then are supplied to non-inverting input portions of comparators $62_1$ to $61_N$. Reference voltages V1 to VN are being supplied respectively to inverting input portions of the comparators $62_1$ to $61_N$. The comparator $62i$ (i=1 to N) compares the detection signal Bi with the corresponding reference voltage Vi and outputs a comparison signal Ci which indicates the high level "1" when the detection signal Bi is larger than the reference voltage Vi and indicates the low level "0" when the detection signal Bi is equal to or less than the reference voltage Vi. The comparison signals C1 to CN output from the comparators $42_1$ to $42_N$ are sent to an input portion of a N-input and circuit 49. The and circuit 49 outputs a defect discriminating signal S7 which indicates the high level "1" when all the comparison signals C1 to CN are the high level "1" and indicates the low level "0" in other cases.

In this case, when the defect discriminating signal S7 is the high level "1", it is judged that there is a defect. On the other hand, when the defect discriminating signal S7 is the low level "0", it is judged that there is no defect. Also, the size of the detected defect is judged as follows.

Figure 9:
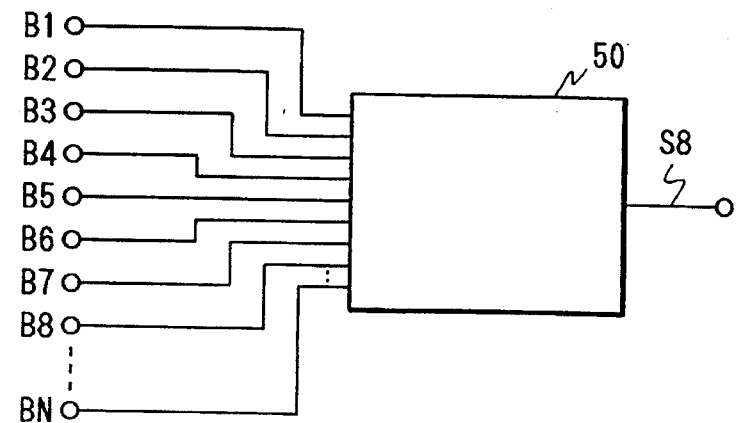
FIG. 9 is a block diagram showing an example of a defect size discriminating circuit of the signal processing system in the third embodiment.

FIG. 9 shows a defect size detecting circuit of the signal processing circuit of this embodiment. In FIG. 9, the detection signals B1 to BN output from the amplifiers $61_1$ to $61_N$ of FIG. 8 are sent to a minimum value selecting circuit 50. The minimum value selecting circuit 50 outputs one of the detection signals B1 to BN having a minimum value as a minimum value signal S8. The defect discriminating circuit in FIG. 8 and the defect size detecting circuit in FIG. 9 operate cooperatively and regard the value of the minimum value signal S8 as the size of the defect when the defect discriminating signal S7 is the high level "1".

Also, in FIG. 7, the shiftable rotating section 23 generates the position information S5 indicating the two-dimensional coordinates of the present inspection point P on the wafer 1 in the xy-plane. The position information S5, the defect discriminating signal S7 and the minimum value signal S8 are supplied to the signal processor 42 (see FIG. 1). The signal processor 42 combines the position information S5, the defect discriminating signal S7 in FIG. 8 and the minimum value signal S8 and displays the positions and sizes of defects on the surface of the wafer on the screen of a display (not shown) in the form of a map.

When there is the non-equality of the Fourier spectrum on the rear focal plane 33 in FIG. 7, there is a case that the energy of the light flux chiefly including the information of defect portions which passes through the spatial filter 34 is modulated owing to the rotation of the disk-like spatial filter 34. Such energy modulation affects the detection of defects and the discrimination of the sizes thereof. As this energy modulation is in synchronism with the rotation of the spatial filter 34, its influence can be canceled in the following manner. That is, while a sample (minute beads in a predetermined shape) for correction to be the reference of a defect is applied to a plain wafer, or a light source for correction is provided in a position conjugate to the inspection point P, detection signals of the photoelectric converting devices $40_1$ to $40_N$ are recorded, whereby the energy modulation is measured as a function of the rotation angle of the spatial filter 34. And, gains of the amplifiers $61_1$ to $61_N$ in FIG. 8 should be modulated so as to cancel the energy modulation. Thereby, it is possible to inspect the wafer 1 constantly with the same defect detecting sensitivity.

Next, the structures of the spatial filter 34 in FIG. 7 and the set of optical fiber handles $38_1$ to $38_N$ for the wavefront splitting will be described. In this embodiment, instead of forming respective optimum spatial filters for the various circuit patterns in the pattern units formed on the wafer, one spatial filter 34 is utilized for the various circuit patterns in the unit patterns. And, the light flux passed through the spatial filter 34 is subjected to the wavefront splitting in the vicinity of the Fourier transform surface and a plurality of spatial frequency components are converted photoelectrically, whereby the intensity distribution of the Fourier spectrum passed through the spatial filter 34 is measured to discriminate the presence or absence of defects.

Figure 10:
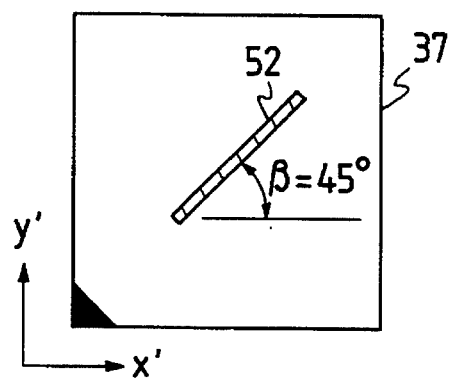
FIG. 10 is an enlarged plan view showing an example of a linear pattern in the pattern unit on the wafer.
Figure 11A:
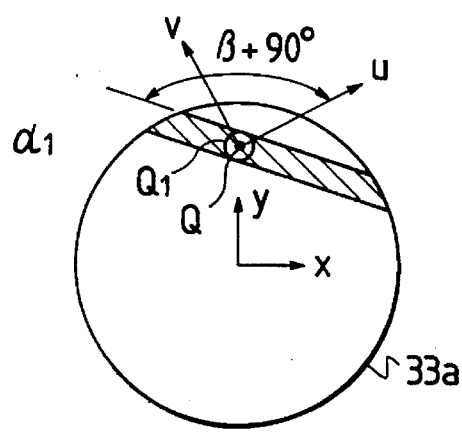
FIGS. 11A, 11B and 11C are explanatory diagrams showing states of Fourier spectrums of the linear patterns of FIG. 10, when the angle formed by the reference coordinate system (x', y') (the coordinate system (u, v) of the Fourier transform plane) and the coordinate system (x, y) of the apparatus is changed.
Figure 11B:
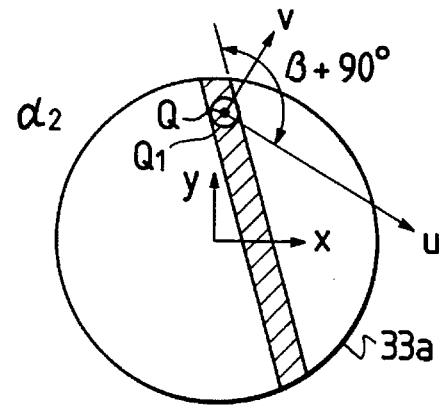
Figure 11C:
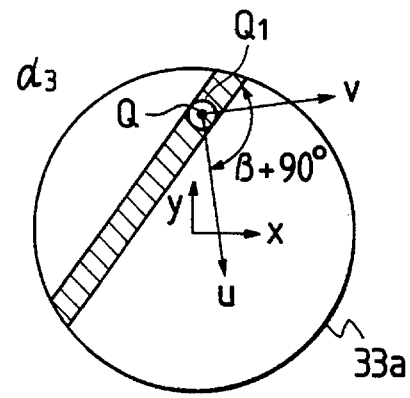

Now, the circuit pattern of the pattern unit 37 rotated at the angle $\alpha_1$, $\alpha_2$ or $\alpha_3$ with respect to the coordinate system (x, y) of the apparatus in FIGS. 3A, 3B or 3C is assumed to be a linear pattern 52 shown in FIG. 10. This linear pattern 52 forms an angle β (β=45° in FIG. 10) with respect to the x'-axis of the reference coordinate system on the pattern unit 37. As shown by hatched portions in FIGS. 11A, 11B and 11C, the Fourier spectrum observed in the spectrum area 33a under this condition is a strip-like pattern perpendicular to a line intersecting the x'-axis of the reference coordinate system in the pattern unit, i.e., the u-axis on the Fourier transform plane at the angle β. The thickness of the strip-like pattern is defined by a spectrum Q1 of the specular light formed on the position Q of the zero-order light component.

Figure 12:
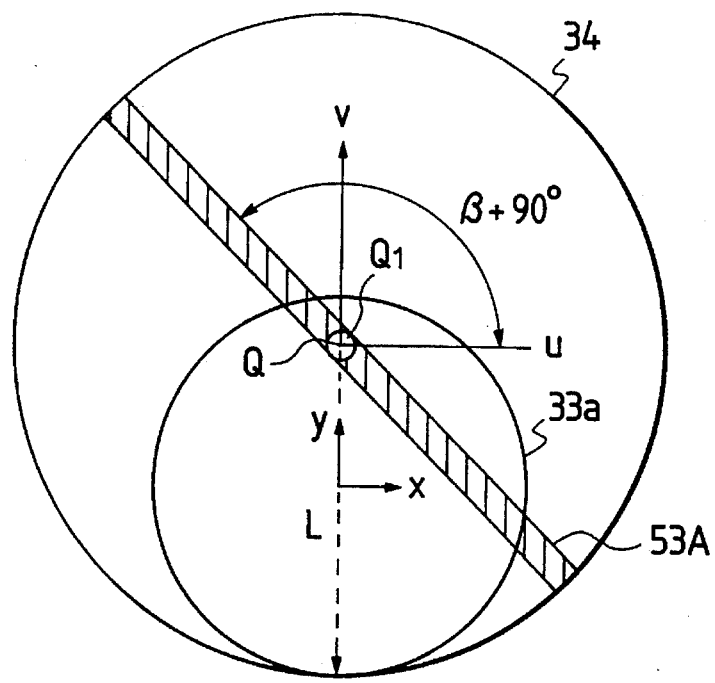
FIG. 12 is a diagram showing a light-shielding zoom 53A for preventing the Fourier transform pattern of the linear pattern in FIG. 10 from filtering.

Therefore, in order to prevent the infiltration of the Fourier spectrum formed by the linear pattern 52 intersecting the x'-axis at the angle β (45°) as shown in FIG. 10, a light-shielding zone 53A is required which consists of a strip-like opaque portion and intersects the u-axis (the x'-axis of the reference coordinate system in the pattern unit) of the Fourier transform plane at the angle of 135° (=90°+β), as shown in FIG. 12.

In addition to the linear pattern 52 in FIG. 10, in the pattern unit 37, there are patterns whose angle β formed with respect to the x'-axis of the reference coordinate system in the pattern unit 37 is 0°, 90° or 135°. For these linear circuit patterns, as shown in FIG. 13, the spatial filter 34 needs to have light-shielding zones 53A to 53D intersecting the u-axis (the x'-axis of the reference coordinate system in the unit pattern) of the Fourier transform plane at the angle of −45°, 0°, 45° and 90° respectively. Therefore, by utilizing the spatial filter 34 of this embodiment, the Fourier transform pattern of the linear patterns included in the ordinary circuit pattern is eliminated, so that this spatial filter 34 can be commonly utilized for various circuit patterns on a wafer.

The light pattern passing through the spatial filter 34 of this embodiment includes the light pattern of defect portions and the light pattern corresponding to patterns arranged two-dimensionally periodically. In this embodiment, in order to discriminate these, the end faces of the optical fiber handles $38_1$ to $38_N$ are disposed in the vicinity of the rear focal plane 33 in FIG. 7 so as to divide the spatial frequency component. The divided respective spatial frequency components are converted photoelectrically to be the detection signals A1 to AN.

Figure 14:
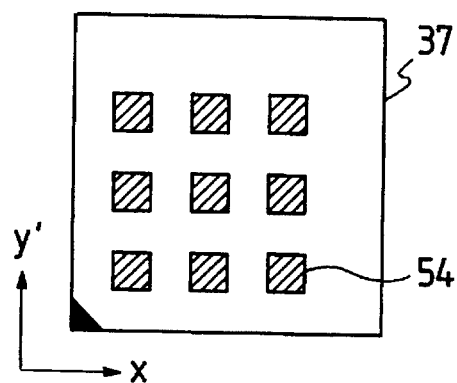
FIG. 14 is an enlarged plan view showing an example of patterns arranged two-dimensionally and periodically in the pattern unit on the wafer.

FIG. 14 shows a circuit pattern 54 in the pattern unit 37, as an example of patterns arranged two-dimensionally periodically in the parallel direction with respect to the reference coordinate system (x', y') in the pattern unit 37. The length of one side of each of rectangular patterns constituting the circuit pattern 54 is about 1 μm to 3 μm. Therefore, there are a plurality of rectangular patterns within the light illuminating the inspection point P in FIG. 7.

Figure 15A:
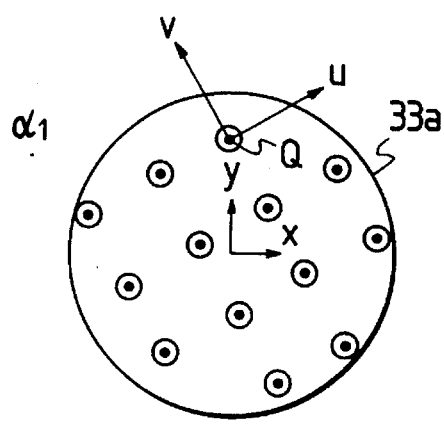
FIGS. 15A, 15B and 15C are explanatory diagrams showing the states of the Fourier spectrums of the pattern in FIG. 14 when the angle formed by the reference coordinate system (x', y') (the coordinate system (u, v) of the Fourier transform plane) and the coordinate system (x, y) of the apparatus is changed.
Figure 15B:
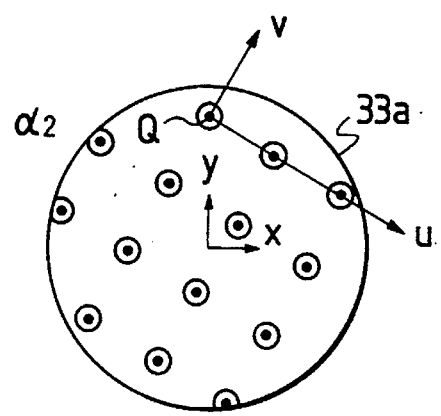
Figure 15C:
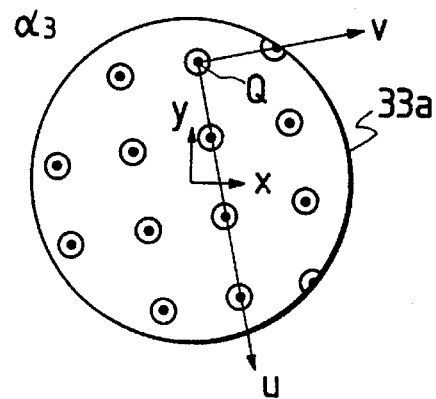
Figure 16:
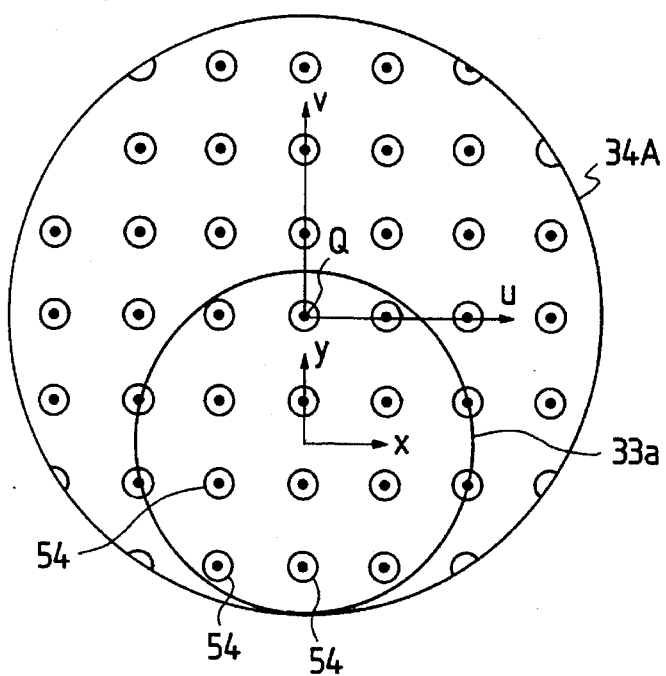
FIG. 16 is a diagram showing the Fourier spectrum of the patterns in FIG. 14 on the Fourier transform plane in FIG. 7.

FIG. 16 shows a discrete Fourier spectrum 54 observed in the spectrum area 33a on the rear focal plane 33 when the reference coordinate system (x', y') in the pattern unit 37 is parallel to the coordinate system (x, y) of the apparatus under the above condition. At this time, with the position Q of the zero-order light component as the origin, the u-axis and v-axis of the spatial frequency component on the Fourier transform plane are defined respectively in parallel to the x'-axis and y'-axis of the reference coordinate system. As shown in FIG. 2, the angle α formed by the reference coordinate system (x', y') in the pattern unit 37 and the coordinate system (x, y) of the apparatus is changed in accordance with the rotation of the wafer 1. As the angle α becomes $\alpha_1$, $\alpha_2$ and $\alpha_3$, the spectrum observed in the spectrum area 33a is rotated around the origin of the position Q together with the coordinate system (u, v) in synchronism with the angle α, as shown in FIGS. 15A, 15B and 15C.

When the angle α formed by the reference coordinate system (x', y') in the pattern unit 37 and the coordinate system (x, y) of the apparatus is changed in the range of 0° to 360°, as shown in FIG. 16, the spectrum observed in the spectrum area 33 is the pattern 54 within a circular area 34A having a predetermined radius with the origin of the position Q as its center. In FIG. 16, the spectrum of the light flux from a defect portion on the wafer 1 in FIG. 7 is generated within the spectrum area 33a approximately uniformly. Therefore, in order to judge in the defect discriminating circuit in FIG. 8 from the energy in each of a plurality of spectrum detecting areas obtained by dividing the spectrum area 33a that there is no defect with respect to the spectrum (e.g., the pattern 54 in FIG. 16) generated when there is no defect and only circuit patterns arranged two-dimensionally and periodically are located on the inspection point P, the light energy being incident on at least one of the plurality of divided spectrum detecting areas should be equal to or less than a predetermined threshold.

Accordingly, the spectrum area 33a should be divided into the plurality of spectrum detecting areas such that the pattern 54 in FIG. 16 will not enter in at least one of them. Various methods for such division can be considered.

Figure 17A:
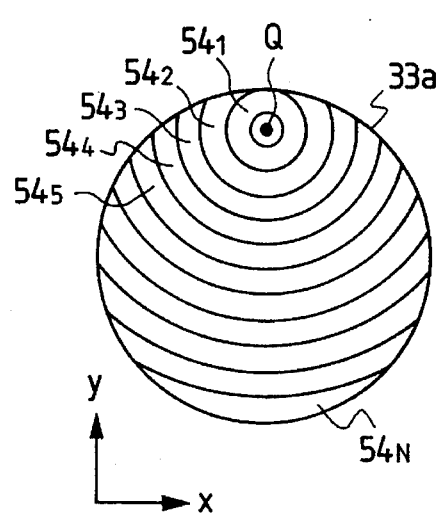
FIG. 17A is a diagram showing an example of a method of dividing the Fourier spectrum area 33a of the Fourier transform lens 31 in FIG. 7.

FIG. 17A shows a dividing method. This dividing method is performed by considering that the Fourier spectrum observed in the spectrum area 33a is rotated around the origin of the position Q by the angular relationship between the coordinate system (x, y) of the apparatus and the reference coordinate system (x', y') in the pattern unit. Therefore, in this dividing method, the spectrum area 33 is divided at regular intervals in the radius direction into N concentric circle-like spectrum detecting portions $54_1$, $54_2$, ..., $54_N$. The one-side end faces of the optical fiber handles $38_1$, $38_2$, ..., $38_N$ (see FIG. 7) are disposed over the spectrum detecting areas $54_N$, $54_{N-1}$, ..., $54_1$ respectively.

Figure 17B:
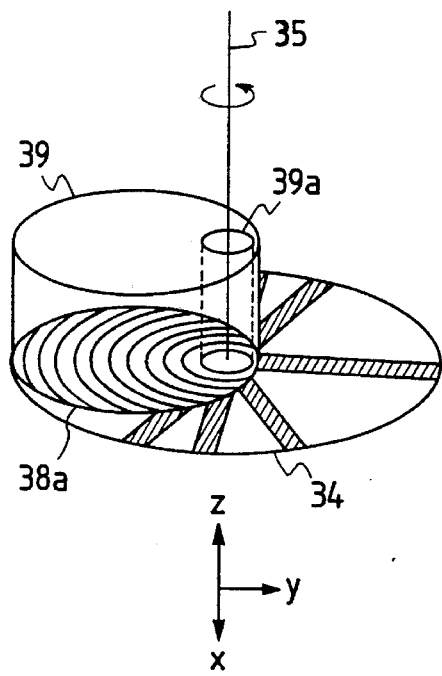
FIG. 17B is a perspective view showing the relationship between the spatial filter 34 in FIG. 7 and the end faces of optical fiber handles when the dividing method in FIG. 17A is adopted.

FIG. 17B is a perspective view showing the relationship between the spatial filter 34 in the coordinate system (x, y, z) of the apparatus, the shaft 35, an end face 38a of the set of optical fiber handles, and the holding member 39 for the set of optical fiber handles. In FIG. 17B, the end faces of the optical fiber handles $38_1$ to $38_N$ in FIG. 7 are disposed in the end face 38a, as shown in FIG. 17A.

According to this embodiment, the inspection point P is rotated and scanned relatively on the wafer 1 at high speed to perform defect inspection on the entire surface of the wafer 1 at high speed. Also, as the Fourier transform pattern of the linear portions of the circuit pattern on the wafer 1 is rotated too owing to the rotation of the wafer 1, the Fourier transform pattern of the patterns of the linear portions is stopped by the use of the spatial filter 34 rotating in synchronism with the rotation of the wafer 1 and the light flux chiefly including defect information passed through the spatial filter 34 is detected to perform the defect detection. Therefore, in the signal processing system, it is sufficient to compare the signals B1 to BN obtained by amplifying the detection signals A1 to AN with the predetermined thresholds, and to maintain the minimum value of the signals B1 to BN in the defect section. Then, since a large computer is not required, the structure of the signal processing system is simple and the processing speed is high.

Also, as shown in FIG. 17A, the spectrum area 33a is divided into the concentric circle-like spectrum detecting portions $54_1$ to $54_N$ and the light pattern of each of the spectrum detecting areas is converted photoelectrically. Accordingly, the probability of the presence of portions among the spectrum detecting portions $54_1$ to $54_N$ wherein the Fourier transform pattern of the linear patterns is not included becomes high, so that the accuracy of detecting defect portions is improved. Also, since the spatial filter 34 can be utilized commonly for various circuit patterns formed on a wafer, it is possible to save time for forming the spatial filter 34.

Figure 18:
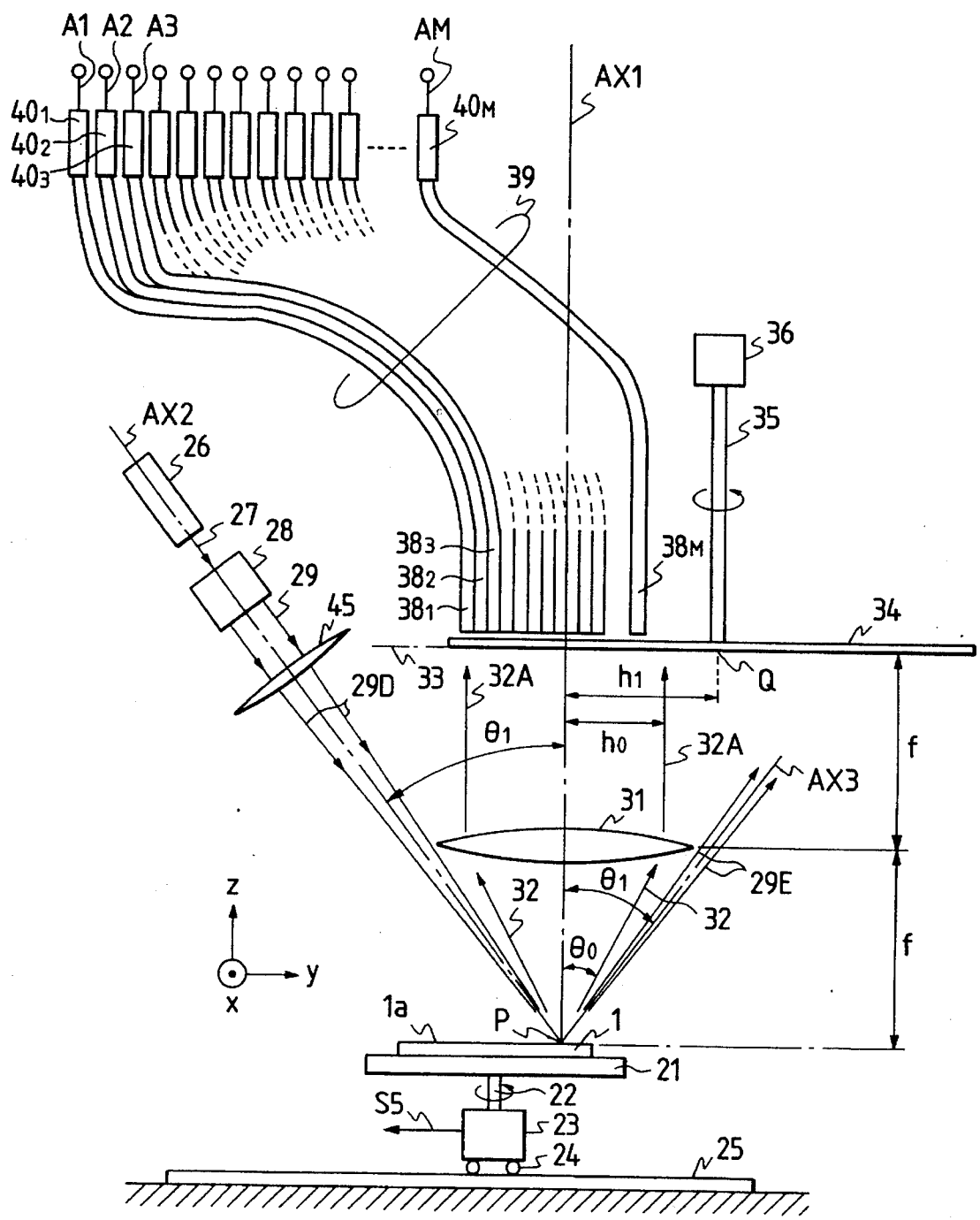
FIG. 18 is a schematic view showing the structure of a rotary type defect inspection apparatus according to a fourth embodiment of the present invention.

Next, a fourth embodiment of the present invention will be described with reference to FIG. 18. In FIG. 18, elements corresponding to those in FIG. 7 are designated by the like reference numerals and then detailed description thereof is omitted.

FIG. 18 shows a rotary type defect inspection apparatus. In FIG. 18, the wafer 1 with the circuit pattern is placed on the turn table 21, which is connected to the shiftable rotating section 23 via the shaft 22. Due to the operation of the shiftable rotating section 23, the wafer 1 is shifted in the y direction while rotating around the shaft 22. Thereby, the round area of light illuminating the inspection point P is rotated relatively on the wafer 1 spirally to scan it. As a result, the defect inspection of the entire surface on the wafer 1 is performed at high speed.

The light flux 27 from the light source 26 disposed above the turn table 21 becomes the parallel light flux 29 having a round cross-sectional shape by means of the beam expander 28 and enters the condensing lens 45. The light flux 29D condensed by the condensing lens 45 illuminates the inspection point P on the wafer 1 as the round area of light with the diameter of, e.g., 30 μm. The Fourier transform lens 31 is disposed above the wafer 1, the effective center of the Fourier transform lens 31 is positioned in a plane spaced at the focal length f from the surface 1a of the wafer 1.

The light flux 32 emanated from the inspection point P due to the light flux 29D enters the Fourier transform lens 31. Then, the selectively filterable Fourier spectrum is formed on the rear focal plane 33 of the Fourier transform lens 31 by the light flux 32A passed through the Fourier transform lens 31.

The Fourier transform lens 31 has the characteristic that in the relationship between the image height h due to the incident light flux and the angle θ formed by the light flux and the optical axis X1, the image height h is proportional to $f \cdot \sin\theta$. The Fourier transform lens 31 has the characteristic that, e.g., $h = f \cdot \sin\theta$. The light flux 32 from the wafer 1 enters the Fourier transform lens 31 at the angle $\theta_0$ with respect to the optical axis AX1 and forms a round area of light on the rear focal plane 33 in a position where the image height $h_0$ is $f \cdot \sin\theta_0$. If the optical axis of the illumination system including the light source 26 and the condensing lens 45 is AX2 and, the optical axis AX2 and the optical axis AX1 intersect at the angle $\theta_1$, the optical axis AX3 of the light flux 29E reflected directly from the surface of the wafer 1 due to the light flux 29D intersects the optical axis AX1 at the angle $\theta_1$.

In this embodiment, the aperture of the Fourier transform lens 31 is not large enough for the light flux from the surface of the wafer 1 being at the angle $\theta_1$ with respect to the optical axis AX1 to enter therein, so that it is impossible to measure the spatial frequency spectrum of the light flux 29E on the rear focal plane 33. However, the angle $\theta_1$ is known in advance, it is apparent that the position of the height $h_1$ ($=f \cdot \sin\theta_1$) from the optical axis AX1 is the spectrum position of the light flux 29E (zero-order light). Therefore, in this embodiment, the spatial filter 34 is rotated around the position Q of the image height $h_1$ on the rear focal plane 33. The structure and operation of the spatial filter 34 are the same as in the first embodiment. The Fourier transform pattern of the linear portions of the nonerroneous circuit pattern is stopped by the light-shielding portion of the spatial filter 34 and the light patterns generated from the circuit patterns arranged two-dimensionally and the defect portions are transmitted through the light transmitting portion of the spatial filter 34.

Also, in this embodiment, while the wafer 1 is rotated and scanned in a similar manner to the third embodiment, the spatial filter 34 is rotated in synchronism with the rotation of the wafer 1 and the Fourier transform pattern of the linear portions of the nonerroneous circuit pattern is stopped. Therefore, the light flux passed through the spatial filter 34 includes the light pattern corresponding to the circuit patterns arranged two-dimensionally and the light pattern corresponding to the defect portions. The light flux passed through the spatial filter 34 is subjected to the wavefront splitting by respective one-side end faces of a set of optical fiber handles $38_1$ to $38_M$ (M=a predetermined integer) in the vicinity of the rear focal plane 33 and thereafter is incident on light receiving surfaces of photoelectric converting element $40_1$ to $40_M$ disposed in opposition to the other-side end faces of the optical fiber handles $38_1$ to $38_M$.

Detection signals A1 to AM converted photoelectrically by the photoelectric converting elements $40_1$ to $40_M$ are supplied to the defect discriminating circuit of the signal processing system the same as in FIG. 8. Thereby, the judgment of the presence or absence of defects and the detection of sizes of defect portions are performed in a similar manner to the third embodiment. The other structure is the same as in the third embodiment, so the description thereof is omitted.

Next, the structure of the spatial filter 34 and the optical fiber handles $38_1$ to $38_M$ for the wavefront splitting of this embodiment will be described.

In this embodiment, similarly to the third embodiment, instead of forming optimum spatial filters for respective circuit patterns in pattern units on a wafer, one spatial filter 34 corresponds to the various circuit patterns. Then, the light flux passed through the spatial filter 34 is subjected to the wavefront splitting in the vicinity of the Fourier transform plane (rear focal plane 33) and the split spatial frequency components are converted photoelectrically to judge the presence or absence of defects.

Figure 19A:
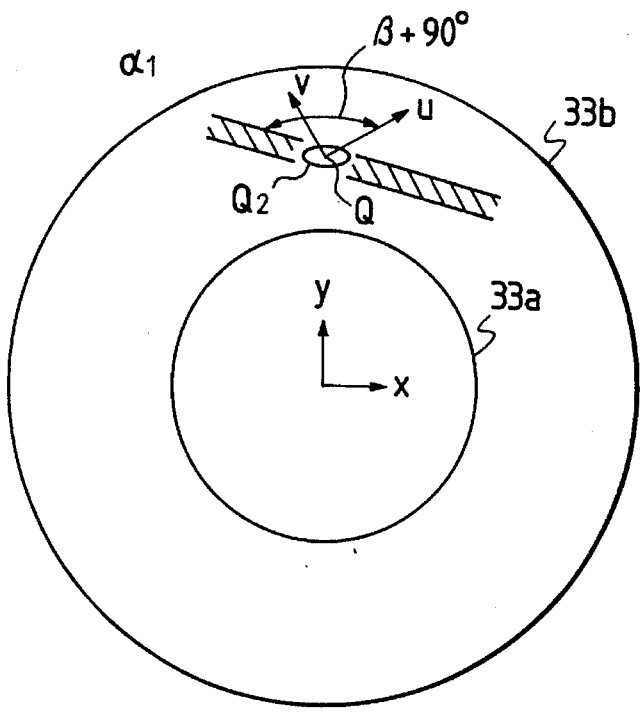
FIGS. 19A, 19B and 19C are explanatory diagrams showing the state of the Fourier spectrums of the linear patterns in FIG. 10 when the angle formed by the reference coordinate system (x', y') (the coordinate system (u, v) of the Fourier transform plane) and the coordinate system (x, y) of the apparatus is changed.
Figure 19B:
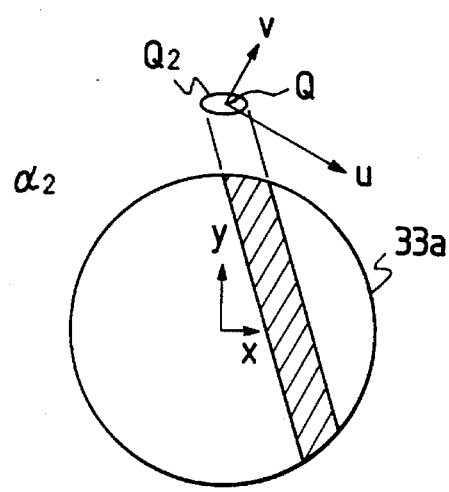
Figure 19C:
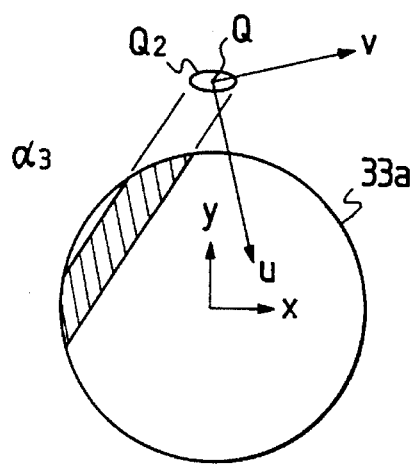

Now, the circuit pattern in the pattern unit 37 rotated respectively at the angle $\alpha_1$, $\alpha_2$ or $\alpha_3$ with respect to the coordinate system (x, y) of the apparatus in FIG. 3A, 3B and 3C is assumed to be the linear pattern 52 shown in FIG. 10. The linear pattern 52 intersects the x'-axis of the reference coordinate system on the pattern unit 37 at the angle $\beta$ ($\beta$=45° in FIG. 10). As shown by hatched portions in FIGS. 19A, 19B and 19C, the Fourier spectrum observed in the spectrum area 33a under this condition is a strip-like pattern perpendicular to a line intersecting the x'-axis of the reference coordinate system in the pattern unit, i.e., the u-axis on the Fourier transform plane at the angle $\beta$. The thickness of the strip-like pattern is defined by an elliptical spectrum Q2 of the specular light formed on the position Q of the zero-order light component.

The spectrum Q2 of the specular light is not located in the spectrum area 33a defined by the Fourier transform lens 31 in FIG. 18. However, if the size of the aperture of the Fourier transform lens 31 in FIG. 18 is enlarged so as to be able to observe in a spectrum area 33b larger than the spectrum area 33a, the spectrum Q2 can be observed. Also, in FIG. 18, as the light flux 29D whose cross section has a round shape is projected to the surface of the wafer 1 diagonally, the spectrum Q2 in FIG. 19 is in the shape of an ellipse.

Figure 20:
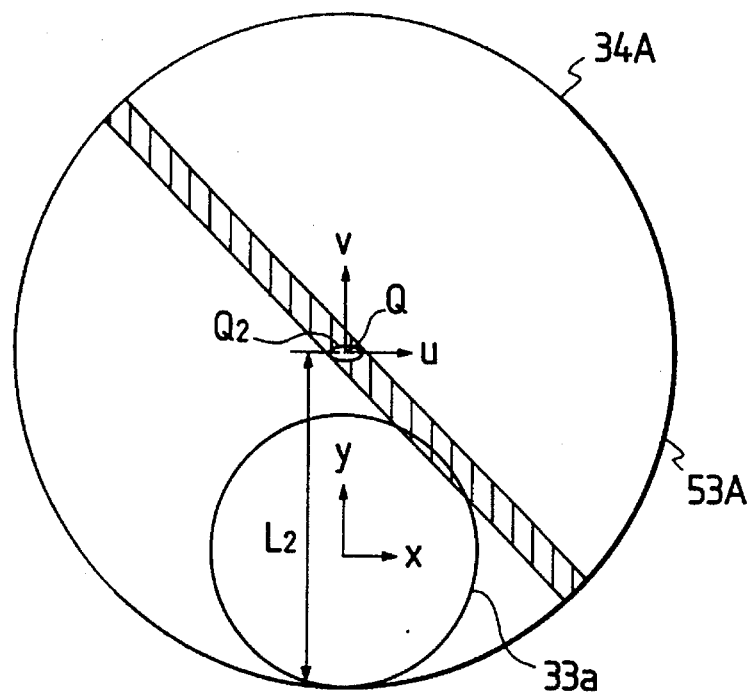
FIG. 20 is a diagram showing the light-shielding zone 53A for preventing the Fourier transform pattern of the linear pattern in FIG. 10 from filtering.

Therefore, in order to prevent the infiltration of the Fourier spectrum generated by the linear pattern 52 intersecting the x'-axis at the angle $\alpha$ (45°) as shown in FIG. 10, the light-shielding zone 53A is required which consists of the strip-like opaque portion and intersects the u-axis (the x'-axis of the reference coordinate system in the pattern unit) of the Fourier transform plane at the angle of 135° (=90°+$\beta$), as shown in FIG. 20. Also, in FIG. 20, if the distance from the position Q of the center of the spectrum Q (zero-order light component) of the specular light to the furthest point of the spectrum area 33 is $L_2$, the size of the spatial filter 34 in FIG. 18 is set so as to cover the circular area 34A having the radius $L_2$ with the position Q as the center.

Figure 21:
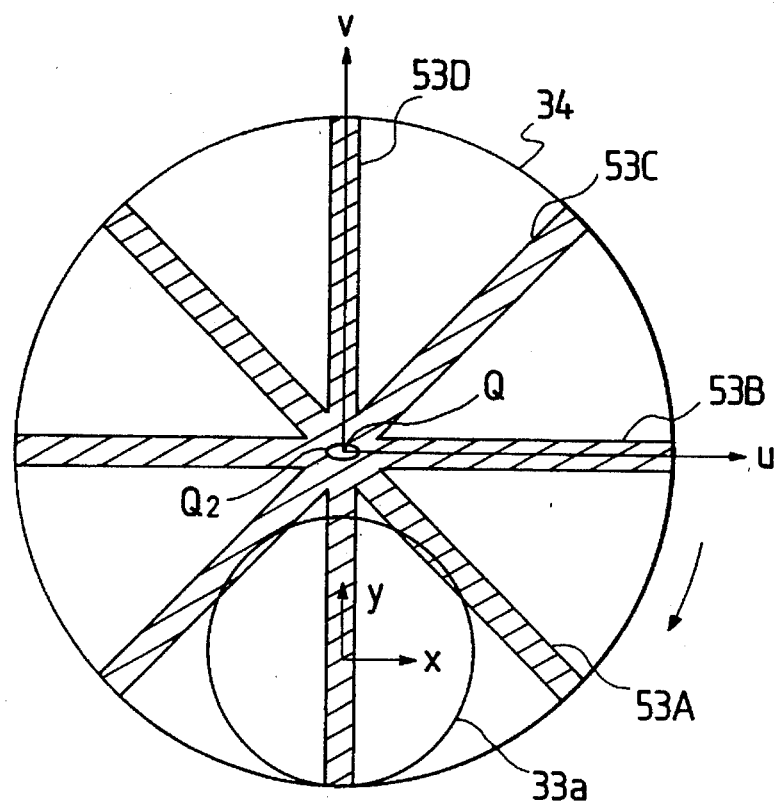
FIG. 21 is a diagram showing the light-shielding zones 53A to 53D for preventing the Fourier transform patterns of linear patterns in various directions.

In addition to the linear pattern 52 in FIG. 10, in the pattern unit 37, there are patterns whose angle $\beta$ formed with respect to the x'-axis of the reference coordinate system in the pattern unit 37 is 0°, 90° or 135°. For these linear circuit patterns, as shown in FIG. 21, the spatial filter 34 needs to have light-shielding zones 53A to 53D intersecting the u-axis (the x'-axis of the reference coordinate system in the unit pattern) of the Fourier transform plane at the angle of −45°, 0°, 45° and 90° respectively. Further, the width of the light-shielding zones 53A to 53D is made to coincide with the major axis of the elliptical spectrum Q of the specular light.

The light pattern passing through the spatial filter 34 in FIG. 21 includes the light pattern of defect portions and the light pattern corresponding to patterns arranged two-dimensionally periodically. In this embodiment, in order to discriminate these, the end faces of the optical fiber handles $38_1$ to $38_M$ are disposed in the vicinity of the rear focal plane 33 in FIG. 18 so as to divide the spatial frequency component. The divided respective spatial frequency components are converted photoelectrically to be the detection signals A1 to AM.

FIG. 14 shows the circuit pattern 54 as an example of patterns arranged two-dimensionally and periodically in the parallel direction to the reference coordinate system (x', y') in the pattern unit 37. The length of one side of each of rectangular patterns constituting the circuit pattern 54 is about 1μm to 3μm. Therefore, there are a plurality of rectangular patterns within the light illuminating the inspection point P in FIG. 7.

Figure 22:
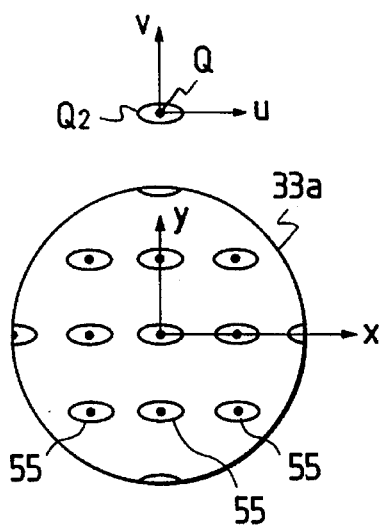
FIG. 22 is a diagram showing the Fourier spectrum of the patterns of FIG. 14 arranged periodically.
Figure 23A:
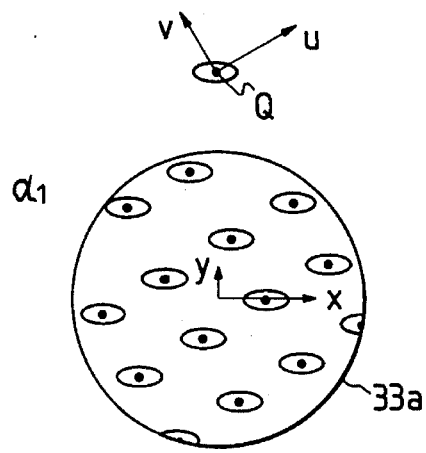
FIGS. 23A, 23B and 23C are explanatory diagrams showing the Fourier spectrums of the pattern in FIG. 14 when the angle formed by the reference coordinate system (x', y') (the coordinate system (u, v) of the Fourier transform plane) and the coordinate system (x, y) of the apparatus is changed.
Figure 23B:
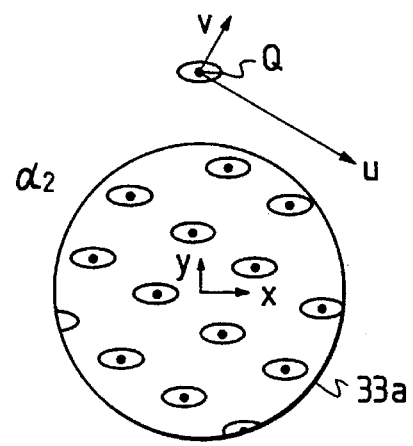
Figure 23C:
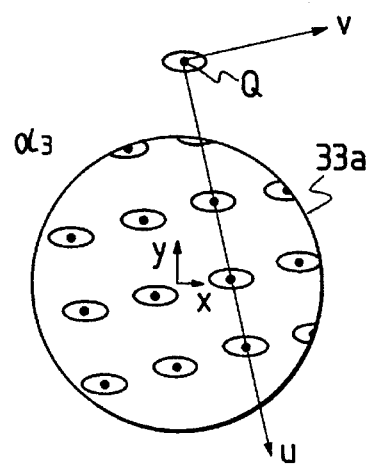

FIG. 22 shows a discrete Fourier spectrum 55 observed in the spectrum area 33a on the rear focal plane 33 when the reference coordinate system (x', y') in the pattern unit 37 is parallel to the coordinate system (x, y) of the apparatus under the above condition. At this time, with the position Q of the zero-order light component as the origin, the u-axis and v-axis of the spatial frequency component on the Fourier transform plane are defined respectively in parallel to the x'-axis and y'-axis of the reference coordinate system. As shown in FIG. 2, the angle $\alpha$ formed by the reference coordinate system (x', y') in the pattern unit and the coordinate system (x, y) of the apparatus is changed in accordance with the rotation of the wafer 1. As the angle $\alpha$ becomes $\alpha_1$, $\alpha_2$ and $\alpha_3$, the spectrum observed in the spectrum area 33a is rotated around the origin of the position Q together with the coordinate system (u, v) in synchronism with the angle $\alpha$, as shown in FIGS. 23A, 23B and 23C.

When the angle $\alpha$ formed by the reference coordinate system (x', y') in the pattern unit and the coordinate system (x, y) of the apparatus is changed in the range of 0° to 360°, as shown in FIG. 20, the spectrum observed in the spectrum area 33a is the pattern within the circular area 34A having the predetermined radius with the origin of the position Q as its center. In FIG. 20, the spectrum of the light flux from a defect portion on the wafer 1 in FIG. 7 is generated within the spectrum area 33a approximately uniformly. Therefore, in order to judge in the defect discriminating circuit the same as in FIG. 8 from the energy in each of a plurality of spectrum detecting areas obtained by dividing the spectrum area 33a that there is no defect with respect to the spectrum (e.g., the pattern 55 in FIG. 22) generated when there is no defect and only circuit patterns arranged two-dimensionally and periodically are located on the inspection point P, the light energy being incident on at least one of the plurality of divided spectrum detecting areas should be equal to or less than a predetermined threshold.

Accordingly, the spectrum area 33a should be divided into the plurality of spectrum detecting areas such that the pattern 55 in FIG. 22 will not enter in at least one of them. Various methods for such division can be considered.

Figure 24A:
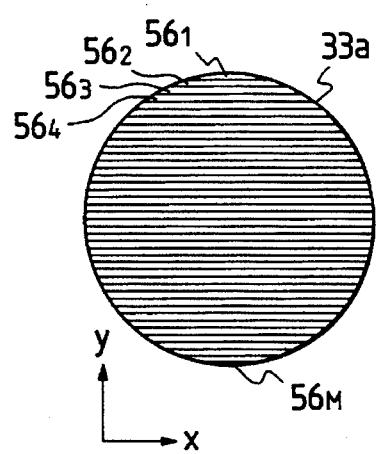
FIG. 24A is a diagram showing a method of dividing the Fourier spectrum area 33a of the Fourier transform lens 31 in FIG. 18.

FIG. 24A shows a dividing method. In this dividing method, not depending on the angular relationship between the coordinate system (x, y) of the apparatus and the reference coordinate system (x', y') of the pattern unit, it is taken into consideration that the Fourier spectrum observed in the spectrum area 33a has the longitudinal direction in the x direction and divided into strip-like areas having the longitudinal direction constantly in the x direction. In FIG. 24A, the circular spectrum area 33a is divided at regular intervals in the y direction into M strip-like spectrum detecting portions $56_1, 56_2, \ldots, 56_M$. Then, the one-side end faces of the optical fiber handles $38_1, 38_2, \ldots, 38_M$ in FIG. 18 are disposed over the M strip-like spectrum detecting portions $56_M, 56_{M-1}, \ldots, 56_1$. Thereby, the Fourier spectrums of the M strip-like spectrum detecting portions $56_1, 56_2, \ldots, 56_M$ in the spectrum area $33a$ are respectively converted by the photoelectric converting devices $40_M, 40_{M-1}, \ldots, 40_1$ in FIG. 18.

Figure 24B:
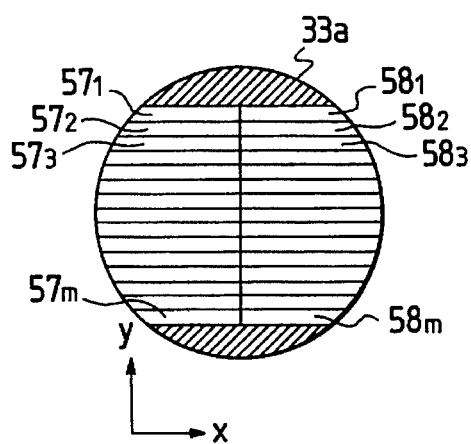
Figure 25:
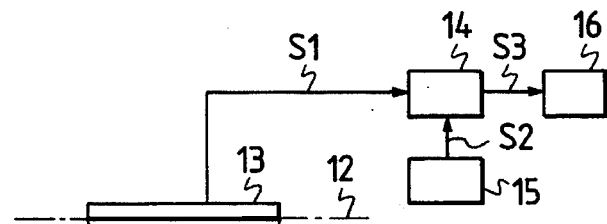
FIG. 25 is a schematic view showing the structure of a conventional defect inspection apparatus.
Figure 25:
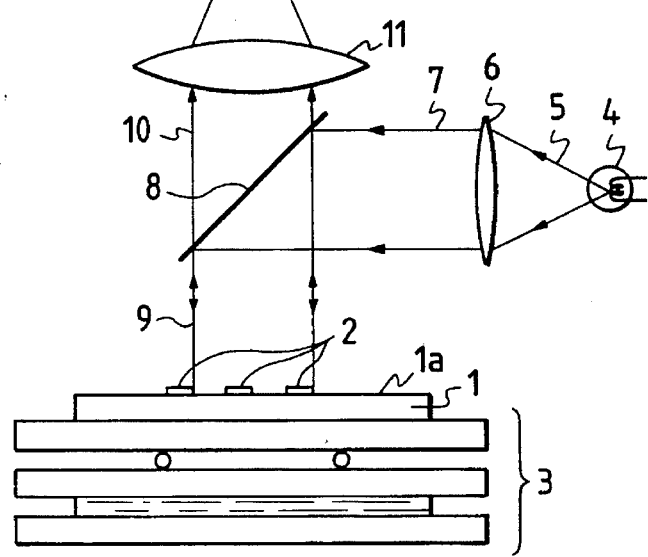

FIG. 24B shows another method of dividing the spectrum area $33a$. In FIG. 24B, the spectrum area $33a$ is divided at predetermined intervals in the y direction into strip-like portions and each of the strip-like portions is divided into two portions, $57_1, 58_1; 57_2, 58_2; \ldots; 57_m, 58_m$. The number M of optical fiber handles $38_1$ to $38_M$ in FIG. 18 is 2 m. One-side end faces of the optical fiber handles $38_1$ to $38_M$ are disposed over the spectrum detecting portions $57_1$ to $57_m$ and $58_1$ to $58_m$. In this case, the spectrum area $33a$ is divided two-dimensionally to such an extent that there is not any portion to which light does not reach via the spatial filter 34 completely.

According to the fourth embodiment, similarly to the third embodiment, while rotating and scanning the wafer 1, the spatial filter 34 is rotated in synchronism with the rotation of the wafer 1 to stop the Fourier transformation patterns from the linear patterns by the spatial filter 34. And, the light flux passed through the spatial filter 34 is converted by the photoelectric converting devices $40_1$ to $40_M$ into the detection signals to detect the positions and sizes of detect portions at high speed. At this time, in this embodiment, the Fourier transform component far away from the zero-order light component as compared to the first embodiment is detected on the rear focal plane 33. Also, the Fourier transform component from the nonerroneous circuit pattern is intense around the zero-order light component generally. Therefore, by extracting the component away from the zero-order light component, the influence of the nonerroneous circuit pattern is reduced to enhance the ability of detecting defect portions.

Also, in the embodiment of FIG. 7, the set of optical fiber handles in FIG. 6 can be utilized instead of the Fourier transform lens 31.

According to the third and fourth embodiments, the substrate to be inspected is rotated and shifted by means of the turn table and the shifting means, so the defect inspection of the entire surface on the substrate can be carried out at high speed. Also, since the position and size of a defect portion are obtained from a signal with a minimum level among photoelectric conversion signals from the set of photoelectric converting means, the structure of the signal processing system is simple and the signal processing speed is high.

Further, when the Fourier transform components from the linear patterns are stopped by rotating the spatial filter in synchronism with the rotation of the substrate, almost all the Fourier transform components of the circuit pattern on the substrate is eliminated, so that the defect inspection can be performed with a high SN-ratio.

Further, when the filter rotating means rotates the spatial filter centered on the position of the zero-order light component of the Fourier transform pattern of the nonerroneous reference pattern, the Fourier transform components from the linear patterns are preferably eliminated.

Further, when the light flux of the spatial frequency component formed by the Fourier transform optical device is led via the set of optical fiber bundles to the photoelectric converting means, a large and high-sensitive photoelectric detector such as a photomultiplier can be utilized as the photoelectric converting means.

When the Fourier transform optical device is formed by grouping together the plurality of optical fiber bundles whose one-side ends are disposed on the spherical plane with the predetermined inspection area as its center and whose other-side ends thereof are disposed on a similar position to the orthographic projection of their one-side ends to a predetermined plane, it is possible to bring the Fourier transform optical device near the substrate, enabling miniaturization of the apparatus. And, the light flux emanated from the substrate at a large diffraction angle can be received also to enhance the light receiving efficiency.

It will be understood that various changes and modifications may be made in the form, details and arrangement of the parts without departing from the scope of the invention set forth in the accompanying claims.

What is claimed is:

1. A defect inspection apparatus for detecting defects on a surface of a substrate with a predetermined pattern formed thereon comprising:

illuminating means for emitting light flux for inspection to a predetermined inspection area on the surface of said substrate;

a Fourier transform optical device for performing Fourier transform of the light flux reflected from said substrate, an optical axis of said Fourier transform optical device intersecting a direction of the specular light of the light flux reflected from the surface of said substrate;

a spatial filter disposed in the vicinity of a Fourier transform plane caused by said Fourier transform optical device, portions of said spatial filter coinciding with bright portions of a Fourier transform pattern of a nonerroneous reference pattern obtained by forming said circuit pattern on said substrate so as to have no defect being made to be a light-shielding portion;

photoelectric converting means for converting light flux passed through said spatial filter photoelectrically;

a turn table for rotating said substrate centered on a shaft parallel to the optical axis of said Fourier transform optical device;

filter rotating means for rotating said spatial filter centered on a predetermined shaft in synchronism with rotation of said turn table; and shifting means for shifting said substrate in a plane perpendicular to the optical axis of said Fourier transform optical device, wherein said surface of said substrate is scanned in said predetermined inspection area spirally by rotating and shifting said substrate by said turn table and said shifting means respectively, said spatial filter is rotated by said filter rotating means in synchronism with rotation of said substrate, and defects of said predetermined pattern on said substrate are detected by a photoelectric conversion signal output from said photoelectric converting means.

2. An apparatus according to claim 1, wherein said filter rotating means rotates said spatial filter centered on the position of a zero-order light component of said Fourier transform pattern of said nonerroneous reference pattern.

3. An apparatus according to claim 1, wherein said Fourier transform optical device is formed by grouping together a plurality of optical fiber bundles whose one-side ends are disposed on a spherical plane with said predetermined inspection area as its center and whose other-side ends are disposed on a similar position to an orthographic projection of said one-side ends on a predetermined plane.

4. A defect inspection apparatus for detecting defects on a surface of a substrate with a predetermined pattern formed thereon comprising:

illuminating means for emitting light flux for inspection to a predetermined inspection area on the surface of said substrate;

a Fourier transform optical device for decomposing the light flux reflected from said substrate into spatial frequency component;

a set of photoelectric converting means for receiving the light flux of said spatial frequency components generated by said Fourier transform optical device in light receiving surfaces of a predetermined size and converting the received light flux photoelectrically;

a turn table for rotating said substrate centered on a shaft parallel to an optical axis of said Fourier transform optical device; and shifting means for shifting said substrate in a plane perpendicular to the optical axis of said Fourier transform optical device, wherein said surface of said substrate is scanned in said predetermined inspection area spirally by rotating and shifting said substrate by said turn table and said shifting means respectively, and a defect of said predetermined pattern on said substrate is detected by a signal having a minimum level among photoelectric conversion signals output from said set of photoelectric converting means.

5. An apparatus according to claim 4, further comprising:

a spatial filter disposed in the vicinity of a Fourier transform plane caused by said Fourier transform optical device, a portion of said spatial filter coinciding with a Fourier transform pattern of a linear pattern formed along a predetermined direction being made to be a light-shielding portion and the other left portion of said spatial filter being made to be a light transmitting portion; and filter rotating means for rotating said spatial filter centered on a predetermined shaft in synchronism with rotation of said turn table, wherein light flux passed through said spatial filter is converted photoelectrically by said set of photoelectric converting means while said spatial filter is rotated by said filter rotating means in synchronism with rotation of said substrate.

6. An apparatus according to claim 4, wherein said filter rotating means rotates said spatial filter centered on the position of a zero-order light component of said Fourier transform pattern of said linear pattern.

7. An apparatus according to claim 4, wherein the light flux of said spatial frequency components generated by said Fourier transform optical device is led to said set of photoelectric converting means via a set of optical fiber bundles.

8. An apparatus according to claim 4, wherein said Fourier transform optical device is formed by grouping together a plurality of optical fiber bundles whose one-side ends are disposed on a spherical plane with said predetermined inspection area as its center and whose other-side ends are disposed on a similar position to an orthographic projection of said one-side ends on a predetermined plane.

\* \* \* \* \*